(12) United States Patent
Nakamura et al.

(10) Patent No.: US 7,771,723 B2
(45) Date of Patent: *Aug. 10, 2010

(54) REMEDIES FOR MYELOMA TO BE USED TOGETHER WITH NITROGEN MUSTARD ANTITUMOR AGENTS

(75) Inventors: Akito Nakamura, Shizuoka (JP); Kenichi Akamatsu, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 331 days.

This patent is subject to a terminal disclaimer.

(21) Appl. No.: 10/749,538

(22) Filed: Dec. 30, 2003

(65) Prior Publication Data

US 2004/0247621 A1 Dec. 9, 2004

Related U.S. Application Data

(63) Continuation of application No. 09/202,802, filed as application No. PCT/JP97/02246 on Jun. 27, 1997, now Pat. No. 6,692,742.

(30) Foreign Application Priority Data

Jun. 27, 1996 (JP) .................................. 8-167325

(51) Int. Cl.
*A61K 38/00* (2006.01)
(52) U.S. Cl. .................................. 424/145.1; 424/130.1
(58) Field of Classification Search ........................ None
See application file for complete search history.

(56) References Cited

U.S. PATENT DOCUMENTS

| | | | | |
|---|---|---|---|---|
| 4,738,843 | A | 4/1988 | Oguchi et al. | .................. 424/85 |
| 4,863,902 | A | 9/1989 | Amagase et al. | .............. 514/12 |
| 5,795,965 | A | 8/1998 | Tsuchiya et al. | |
| 5,882,941 | A | 3/1999 | Essigmann et al. | ........ 435/172.1 |

FOREIGN PATENT DOCUMENTS

| | | |
|---|---|---|
| EP | 0 409 607 | 1/1991 |
| EP | 0628639 | 12/1994 |
| WO | WO 92/19759 | 11/1992 |
| WO | WO-03/070234 | 8/2003 |

OTHER PUBLICATIONS

Moreau et al., Blood, Jan. 1, 2006;107(1):397-403.*
Dancey et al., Nature Reviews: Drug Discovery, Aug. 2006;5(8):649-59.*
Anthes et al., *Biochem* (1995) 309(1):175-180.
Budavari et al. (Eds), *The Merck Index: An Encyclopedia of Chemicals, Drugs and Biologicals* (1996) 12th ed.; Whitehouse Station, NJ pp. 344,463,841-842, 984, 993.
Evans et al., *Cancer Chemo Pharmaco* (1982) 8(2):175-178.
Manning et al., *Immun Cell Biol* (1995) 73(4):326-332.
Sarosy et al., *J Clin Oncol* (1988) 7(11):1768-1782.
Sato et al., *Cancer Res* (1993) 53(4):851-856.
Sato et al., *Mol Immunol* 31(5):371-381.
Suzuki et al., *Eur J Immunol* (1992) 22:1989-1993.
Suzuki et al.,*Immun Letts* (1991) 30:17-21.
Tsunenari et al., *Blood* (1997) 90(6):2437-2444.
Daveau et al., Eur. Cytokine Netw. (1994) 5(6):601-608.
Rihova, Advanced Drug Delivery Reviews (1998) 29:273-289.
Goodman & Gilman's The Pharmacological Basis of Therapeutics, Tenth Edition, Hardman et al. (eds.), McGraw-Hill Medical Publishing Division (2001) pp. 1383-1397.
Berenbaum, Clin. Exp. Immunol. (1977) 28:1-18.
Paul, Fundamental Immunology, 3rd ed., (1993) pp. 292-295.
Rudikoff et al., PNAS USA (1982) 79:1979-1983.
Liautard et al., Eur. Cytokine Netw. (1994) 5:293-300.
Pound et al., International Immunology (1998) 11:11-20.
Satata et al., Cellular Immunology (2000) 201:109-123.

* cited by examiner

*Primary Examiner*—Misook Yu
(74) *Attorney, Agent, or Firm*—Morrison & Foerster LLP

(57) ABSTRACT

A therapeutic agent for myeloma comprising a combined use of a nitrogen mustard anticancer agent and anti-IL-6 receptor antibody. Thus, a therapeutic agent for myeloma comprising anti-IL-6 receptor antibody for use in combination with a nitrogen mustard anticancer agent; a therapeutic agent for myeloma comprising a nitrogen mustard anticancer agent for use in combination with anti-IL-6 receptor antibody; and a therapeutic agent for myeloma comprising a nitrogen mustard anticancer agent and anti-IL-6 receptor antibody.

19 Claims, 13 Drawing Sheets

IN THE PRESENCE OF IL-6 (0.1 ng/ml)

IN THE PRESENCE OF IL-6 (1 ng/ml)

IN THE PRESENCE OF IL-6 (0.1 ng/ml)

CONCENTRATION OF ANTI-HUMAN IL-6 RECEPTOR ANTIBODY (µg/ml)

IN THE PRESENCE OF IL-6 (1 ng/ml)

CONCENTRATION OF ANTI-HUMAN IL-6 RECEPTOR ANTIBODY (µg/ml)

REMEDIES FOR MYELOMA TO BE USED TOGETHER WITH NITROGEN MUSTARD ANTITUMOR AGENTS

CROSS-REFERENCE TO RELATED APPLICATION

This patent application claims the benefit of U.S. patent application Ser. No. 09/202,802 filed Dec. 22, 1998, which claims priority to international application no. PCT/JP97/02246 filed Jun. 27, 1997, which claims priority to Japanese application no. 8-167325 filed Jun. 27, 1996. Each of these patent applications is hereby incorporated herein by reference in their entirety, including all drawings and cited publications and documents.

TECHNICAL FIELD

The present invention relates to a pharmaceutical composition for combined use of nitrogen mustard anticancer agents with anti-IL-6 receptor antibody for treatment of myeloma.

BACKGROUND ART

For chemotherapy of human tumors, alkylating agents, antimetabolites, antitumor antibiotics, platinum compounds and the like have been used. When single uses of these activating agents do not exhibit marked therapeutic effects, therapies in which multiple drugs are used in combination have been considered (Frei, E. III, Cancer Res. (1992) 32, 2593-2607). As anticancer agents that belong to the alkylating agents, there are mentioned nitrogen mustard anticancer agents, which is a general term used for the anticancer agents that have a partial structure called nitrogen mustard. Of the nitrogen mustard anticancer agents melphalan has been put into practical use.

IL-6 is a multifunctional cytokeine called B-cell stimulatory factor 2 or interferon β2. IL-6 was discovered as a differentiation factor responsible for activation of B-lymphocytes (Hirano, T. et al., Nature (1986) 324, 73-76). Thereafter, it was found to be a multifunctional cytokeine that influences the function of various cells (Akira, S. et al., Adv. in Immunology (1993) 54, 1-78). IL-6 imparts its biological activity through two proteins on the cell membrane.

One of them is a ligand-biding protein with a molecular weight of about 80 kD, IL-6 receptor, to which IL-6 binds. IL-6 receptor occurs not only in a membrane-bound form that penetrates and is expressed on the cell membrane but also as a soluble IL-6 receptor consisting mainly of the extracellular region. The other is non-ligand-binding gp130 with a molecular weight of about 130 kD that takes part in signal transmission. IL-6 and IL-6 receptor form a IL-6/IL-6 receptor complex, to which another membrane protein gp130 is bound, and thereby the biological activity of IL-6 is transmitted to the cell (Taga et al., J. Exp. Med. (1987) 166, 967).

Antibodies to IL-6 receptor (anti-IL-6 receptor antibodies) have been known (Novick D. et al., Hybridoma (1991) 10, 137-146 Huang, Y. W. et al., Hybridoma (1993) 12, 621-630 International Patent Application WO95-09873, French Patent Application FR 2694767, U.S. Pat. No. 5,216,128), one of which is PM-1 derived from mice (Hirata et al., J. Immunology (1989) 143, 2900-2906). Furthermore, a reshaped antibody obtained by replacing the complementarity determining regions (CDRs) of the mouse antibody with the CDRs of a human antibody has also been known.

However, the combined use of a nitrogen mustard anticancer agent and IL-6 receptor as a therapeutic agent for treatment of myeloma has not been known.

DISCLOSURE OF THE INVENTION

It is an object of the present invention to provide a new type of myeloma therapeutic agent that is more effective than the conventionally known myeloma therapeutic agents.

As a result of an intensive study to solve the above problems, the applicants have found that the combination of a nitrogen mustard anticancer agent, a conventionally known anticancer agent, and anti-IL-6 receptor antibody has a synergistic effect, i.e. it is more effective than the sole use of the nitrogen mustard anticancer agent or the sole use of anti-IL-6 receptor antibody for treatment of myeloma, and have completed the present invention.

Thus, the present invention provides a therapeutic agent for treatment of myeloma comprising anti-IL-6 receptor antibody for use in combination with a nitrogen mustard anticancer agent.

The present invention also provides a therapeutic agent for treatment of myeloma comprising anti-IL-6 receptor monoclonal antibody for use in combination with a nitrogen mustard anticancer agent.

The present invention also provides a therapeutic agent for treatment of myeloma comprising PM-1 antibody for use in combination with a nitrogen mustard anticancer agent.

The present invention also provides a therapeutic agent for treatment of myeloma comprising a reshaped PM-1 antibody for use in combination with a nitrogen mustard anticancer agent.

The present invention also provides a therapeutic agent for treatment of myeloma comprising anti-IL-6 receptor antibody for use in combination with mechlorethamine, nitrogen mustard N-oxide, melphalan, uramustin, ifosfamide, chlorambucil, or cyclophosphamide.

The present invention also provides a therapeutic agent for treatment of myeloma comprising a reshaped human PM-1 antibody for use in combination with melphalan.

The present invention also provides a therapeutic agent for treatment of myeloma comprising a nitrogen mustard anticancer agent for use in combination with anti-IL-6 receptor antibody.

The present invention also provides a therapeutic agent for treatment of myeloma comprising a nitrogen mustard anticancer agent for use in combination with anti-IL-6 receptor monoclonal antibody.

The present invention also provides a therapeutic agent for treatment of myeloma comprising a nitrogen mustard anticancer agent for use in combination with PM-1 antibody.

The present invention also provides a therapeutic agent for treatment of myeloma comprising a nitrogen mustard anticancer agent for use in combination with a reshaped human PM-1 antibody.

The present invention also provides a therapeutic agent for treatment of myeloma comprising mechlorethamine, nitrogen mustard N-oxide, melphalan, uramustin, ifosfamide, chlorambucil, or cyclophosphamide in combination with anti-IL-6 receptor antibody.

The present invention also provides a therapeutic agent for treatment of myeloma comprising melphalan for use in combination with a reshaped human PM-1 antibody.

The present invention also provides a therapeutic agent for treatment of myeloma comprising a nitrogen mustard anticancer agent and anti-IL-6 receptor antibody.

The present invention also provides a therapeutic agent for treatment of myeloma comprising a nitrogen mustard anticancer agent and anti-IL-6 receptor monoclonal antibody.

The present invention also provides a therapeutic agent for treatment of myeloma comprising a nitrogen mustard anticancer agent and PM-1 antibody.

The present invention also provides a therapeutic agent for treatment of myeloma comprising a nitrogen mustard anticancer agent and a reshaped human PM-1 antibody.

The present invention also provides a therapeutic agent for treatment of myeloma comprising mechlorethamine, nitrogen mustard N-oxide, melphalan, uramustin, ifosfamide, chlorambucil, or cyclophosphamide and anti-IL-6 receptor antibody.

The present invention provides a therapeutic agent for treatment of myeloma comprising melphalan and a reshaped human PM-1 antibody.

EMBODIMENTS FOR CARRYING OUT THE INVENTION

Figure 1:
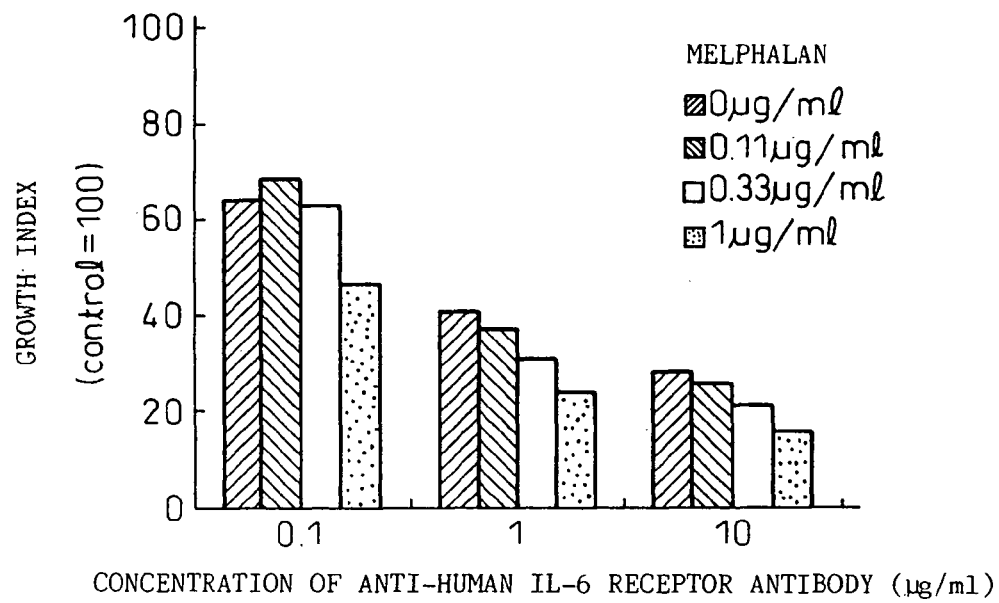
FIG. 1 is a graph showing the relationship of anti-human IL-6 receptor antibody concentration and melphalan concentration with the growth (incorporation of $^3$H-labeled thymidine) of a human myeloma cell line in the presence of 0.1 ng/ml IL-6.

Nitrogen mustard anticancer agents for use in the present invention is a general term for the anticancer agents having a partial structure called nitrogen mustard having the structure:

examples of which agents include:

Mechlorethamine,

Nitrogen mustard N-oxide (methyl-bis(β-chloroethyl) amine N-oxide hydrochloride), Melphalan (p-[bis(2-chloroethyl)amino-L-phenylalanine), Chlorambucil (p-bis(2-chloroethyl)amino-phenylbutyric acid), Uramustin (5-bis(2-chloroethyl)aminouracil), Ifosmide(N,N'-bis(2-chloroethyl)-N', O-propylenephosphoric acid ester diamide Cyclophosphamide(N,W-bis(A-chloroethyl)-N', O-propylenephosphoric acid ester diamide, and the like.

In accordance with the present invention, these nitrogen mustard anticancer agents may be used as a single drug or in combination. Among them, melphalan is also called sarcolysine or L-phenylalanine mustard and has the following structure:

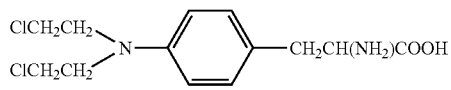

Mechlorethamine can be obtained by a known method, for example, a method described in Abrams et al., J. Soc. Chem. Ind. (London) (1949) 68, 280.

Nitrogen mustard N-oxide can be obtained by a known method, for example, a method described in Aiko'et al., J. Pharm. Soc. Japan (1952) 72, 1297.

Melphalan can be obtained by a known method, for example, a method described in Bergel, F. et al., J. Chem. Soc. (1954) 2409.

Chlorambucil can be obtained by a known method, for example, a method described in Balazc, M. K. et al., J. Pharm. Sci. (1970) 59, 563.

Uramustin can be obtained by a known method, for example, a method described in Lyttle and Petering, J. Am. Chem. Soc. (1958) 80, 6459.

Ifosfamide can be obtained by a known method, for example, a method described in Arnold H. et al., U.S. Pat. No. (1973 to Asta) 3,732,340, or Brassfield, H J. A. et al., J. Am. Che. Soc. (1975) 97, 4143.

Cyclophosphamide can be obtained by a known method, for example, a method described in Arnold H. et al., Angew. Chem. (1958) 70, 539.

1. Anti-IL-6 Receptor Antibody

Anti-IL-6 receptor antibodies for use in the present invention may be of any origin, any kind (monoclonal or polyclonal), and any form, as long as they have a higher therapeutic effect for myeloma when administered in combination with a nitrogen mustard anticancer agent than when an anti-IL-6 receptor antibody alone is administered or when a nitrogen mustard anticancer agent alone is administered.

Anti-IL-6 receptor antibodies for use in the present invention can be obtained as polyclonal or monoclonal antibodies using a known method. As the anti-IL-6 receptor antibodies for use in the present invention, monoclonal antibodies of, in particular, a mammalian origin, are preferred. Monoclonal antibodies of a mammalian origin include those produced by a hybridoma and recombinant antibody produced by a host which has been transformed with an expression vector containing genetically engineered antibody genes. Anti-IL-6 receptor antibodies for use in the present invention, via binding to IL-6 receptor, block the binding of IL-6 to IL-6 receptor, and thereby inhibit signal transmission of IL-6, and therefore are antibodies which inhibit the biological activity of IL-6.

Examples of such antibodies include PM-1 antibody (Hirata, et al., J. Immunology (1989) 143, 2900-2906), or AUK12-20 antibody, AUK64-7 antibody or AUK146-15 antibody (International Patent Application WO 92-19759), and the like. Of them, PM-1 antibody is most preferred.

Incidentally, the hybridoma cell line which produces PM-1 antibody has been internationally deposited under the provisions of the Budapest Treaty as PM-1 on Jul. 10, 1990 with the National Institute of Bioscience and Human Technology, Agency of Industrial Science and Technology, of 1-3, Higashi 1-chome, Tsukuba-shi, Ibaraki, Japan, as FERM BP-2998.

2. Antibody Produced by Hybridoma

Monoclonal antibodies can be obtained by constructing a hybridoma using basically a known procedure as described bellow. Thus, IL-6 receptor is used as an immunizing antigen and is immunized in the conventional method of immunization. The immune cells thus obtained are fused with known parent cells in the conventional cell fusion process, and then screened by the conventional screening method to screen monoclonal antibody-producing cells.

Specifically, monoclonal antibodies may be obtained in the following manner.

For example, IL-6 receptor used as the immunizing antigen for obtaining antibody is not limited to any animal species, but IL-6 receptor derived from humans is particularly preferred. For human IL-6 receptor, IL-6 receptor protein can be obtained using a gene sequence disclosed in European Patent Application EP 325474. There are two kinds of IL-6 receptor: IL-6 receptor expressed on the cell membrane, and IL-6 receptor detached from the cell membrane (Soluble IL-6 Receptor; Yasukawa et al., J. Biochem. (1990) 108, 673-676).

Soluble IL-6 receptor is composed mainly of the extracellular region of IL-6 receptor bound to the cell membrane, and soluble IL-6 receptor is different from the membrane-bound IL-6 receptor in that the former lacks the transmembrane region or both of the transmembrane region and the intracellular region. In accordance with the present invention, IL-6 receptor used as the immunizing antigen may be either the membrane-bound or the soluble IL-6 receptor. Alternatively, it may be a mutant thereof.

After a gene encoding IL-6 receptor is inserted into a known expression vector to transform an appropriate host cell, the desired IL-6 receptor protein is purified from the host cell or a culture supernatant thereof using a known method, and the IL-6 receptor protein thus purified may be used as the immunization antigen. Alternatively, cells that express IL-6 receptor protein may be used as the immunization antigen.

Preferably mammals to be immunized with the immunization antigen are selected in consideration of their compatibility with the parent cells for use in cell fusion and they generally include, but are not limited to, rodents, logomorphas, and primates.

As rodents, for example, mice, rats, hamsters, etc. are used. As logomorphas, for example, rabbits are used. As primates, for example, monkeys are used. As monkeys, catarrhines (Old-World monkeys) such as cynomolgi (crab-eating macaque), rhesus monkeys, sacred baboons, chimpanzees etc. are used.

Immunization of animals with an immunization antigen is carried out using a known method. A general method, for example, involves intraperitoneal or subcutaneous administration of an immunization antigen to the mammal. Specifically, an immunization antigen which was diluted and suspended in an appropriate amount of phosphate buffered saline (PBS) or physiological saline etc. is mixed with an appropriate amount of Freund's complete adjuvant. After being emulsified, it is preferably administered to a mammal for several times every 4 to 21 days. Additionally a suitable carrier may be used at the time of immunization of the immunization antigen.

After the immunization and confirmation of the increase in the desired antibody levels in the serum by a conventional method, immune cells are taken out from the mammal and are subjected to cell fusion, in which especially preferred immune cells are the spleen cells.

The mammalian myeloma cells as the other parent cells which are subjected to cell fusion with the above-mentioned immune cells preferably include various known cell lines such as P3 (P3x63Ag8.653) (Kearney, J. F. et al., J. Immunol. (1979) 123, 1548-1550), P3x63Ag8U·U1 (Yelton, D. E. et al., Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. and Scheidegger, D., J. Immunol. Methods (1980) 35, 1-21), S194 (Trowbridge, I. S., J. Exp. Med. (1978) 148, 313-323), R210 (Galfre, G. et al., Nature (1979) 217, 131-133) and the like.

Cell fusion between the above immune cells and the myeloma cells may be essentially conducted in accordance with a known method such as is described in Milstein et al. (Galfre, G. and Milstein, C., Methods Enzymol. (1981) 73, 3-46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and an adjuvant such as dimethyl sulfoxide etc. may be added as desired to enhance efficiency of the fusion.

The preferred ratio of the immune cells and the myeloma cells for use is, for example, 1 to 10 times more immune cells than the myeloma cells. Examples of culture media to be used for the above cell fusion include RPMI 1640 medium and MEM culture medium suitable for the growth of the above myeloma cell lines, and the conventional culture medium used for this type of cell culture, and besides a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of 1000 to 6000, is added at a concentration of 30 to 60% (w/v) and mixed to obtain the desired fusion cells (hybridomas). And then by repeating a sequential addition of a suitable culture liquid and centrifugation to remove the supernatant, cell fusion agents etc. that are undesirable for the growth of the hybridoma can be removed.

Said hybridoma is selected by culturing in the conventional selection medium, for example, HAT culture medium (a culture liquid containing hypoxanthine, aminopterin, and thymidine). Culturing in said HAT culture medium is continued generally for the period of time sufficient to effect killing of the cells other than the desired hybridoma (non-fusion cells), generally several days to several weeks. The conventional limiting dilution method is conducted in which the hybridomas producing the desired antibody are screened and monoclonally cloned.

In addition to obtaining the above hybridoma by immunizing an animal other than the human with an antigen, it is also possible to immunize human lymphocytes in vitro with IL-6 receptor protein or IL-6 receptor protein-expressing cells, and the resulting immunized lymphocytes are fused with a myeloma cell, for example U266, having the ability of dividing permanently to obtain a hybridoma that produces the desired human antibody having the activity of binding to and neutralizing IL-6 receptor (Japanese Post-examined Patent Publication (Kokoku) 1-59878). Furthermore, a transgenic animal having a repertoire of human antibody genes is immunized with the antigen IL-6 receptor or IL-6 receptor-expressing cells to obtain anti-IL-6 receptor antibody-producing cells. The cells are then fused with myeloma cells to obtain hybridomas that are used to obtain human antibody to IL-6 receptor (see International Patent Application WO 92-03918, WO 93-12227, WO 94-02602, WO 94-25585, WO 96-33735 and WO 96-34096).

The monoclonal antibody-producing hybridomas thus constructed can be maintained in the conventional culture liquid, or can be stored for a prolonged period of time in liquid nitrogen.

In order to obtain monoclonal antibodies from said hybridoma, there can be mentioned a method in which said hybridoma is cultured in the conventional method and the antibodies are obtained as the supernatant, or a method in which the hybridoma is transplanted to and grown in a mammal compatible with said hybridoma and the antibodies are obtained as the ascites. The former method is suitable for obtaining highly purified antibodies, whereas the latter is suitable for a large scale production of antibodies.

In addition to using a hybridoma for antibody production, immune cells such as antibody-producing immunized lymphocytes which has been immortalized with an oncogene can be used.

3. Recombinant Antibody

Monoclonal antibodies may be also obtained as a recombinant antibody which has been produced by the recombinant gene technology. For example, recombinant antibody can be obtained by cloning a gene of an antibody from a hybridoma or an immune cell such as antibody-producing immunized lymphocytes, and then integrated into a suitable vector, which is then introduced into a host to produce said antibody (see, for example, Borrebaeck, C. A. K. and Larrick, J. W., THERAPEUTIC MONOCLONAL ANTIBODIES, published in the United Kingdom by MACMILLAN PUBLISHERS LTD. 1990).

Specifically, mRNA encoding the variable region (V region) of anti-IL-6 receptor antibody is isolated from the hybridoma producing anti-IL-6 receptor antibody. The isolation of mRNA is conducted by preparing total RNA using, for example, a known method such as the guanidine ultracentrifuge method (Chirgwin, J. M. et al., Biochemistry (1979) 18, 5294-5299), the AGPC method (Chomczynski, P. and Sacchi, N., Anal. Biochem. (1987) 162, 156-159), and then mRNA is purified from the total RNA using the mRNA Purification kit (Pharmacia) and the like. Alternatively, mRNA can be directly prepared using the Quick Prep mRNA Purification Kit (Pharmacia).

cDNA of the V region of antibody may be synthesized from the mRNA thus obtained using a reverse transcriptase. cDNA may be synthesized using the AMV Reverse Transcriptase First-strand cDNA Synthesis Kit (Seikagaku Kogyo), and the like. Alternatively, for the synthesis and amplification of cDNA, the 5'-Ampli FINDER RACE Kit.(Clontech) .and the 5'-RACE method (Frohman, M. A. et al., Proc. Natl. Acad. Sci. U.S.A. (1988) 85, 8998-9002; Belyaysky, A. et al., Nucleic Acids Res. (1989) 17, 2919-2932) which employs polymerase chain reaction (PCR) may be used.

The desired DNA fragment is purified from the PCR product obtained and may be ligated to vector DNA. Moreover, a recombinant vector is constructed therefrom and then is transfected into E. coli etc., which is selected to prepare the desired recombinant vector. The base sequence of the desired recombinant vector may be confirmed by a known method such as the dideoxy nucleotide chain termination method.

Once the DNA encoding the V region of the desired anti-IL-6 receptor antibody has been obtained, it may be ligated to DNA encoding the constant region (C region) of the desired antibody, which is then integrated into an expression vector. Alternatively, DNA encoding the V region of the antibody may be integrated into an expression vector which already contains DNA encoding the C region of the antibody. The C region of the antibody may be derived from the same animal species as that of the V region, or from a different animal species from that of the V region.

In order to produce anti-IL-6 receptor antibody for use in the present invention, the antibody gene is integrated into an expression vector so as to be expressed under the control of an expression regulatory region, for example an enhancer and/or a promoter. Subsequently, the expression vector is transformed into a host cell and the antibody is then expressed therein.

The antibody gene may be expressed by integrating separately DNA encoding a heavy chain (H chain) and a light chain (L chain) of the antibody into an expression vector and co-transforming the host cell, or by integrating DNA encoding an H chain and an L chain into a single expression vector and transforming the host cell (International Patent Application WO 94-11523).

4. Altered Antibody

As recombinant antibodies for use in the present invention, artificially altered recombinant antibodies such as chimeric antibody and humanized antibody can be used for the purpose of lowering xenogenic antigenicity against humans. Altered antibodies can have the C regions of human antibody and antibodies such as chimeric antibody or humanized antibody can be used. These altered antibodies can be produced using known methods.

Chimeric antibody can be obtained by ligating the thus obtained DNA encoding the V region of antibody other than human antibody to DNA encoding the C region of human antibody, which is then integrated into an expression vector and introduced into a host for production of the antibody therein (see European Patent Application EP 125023, and International Patent Application WO 92-19759). Using this known method, chimeric antibody useful for the present invention can be obtained.

Plasmid coding for the V region of the L chain or the V region of the H chain of PM-1 antibody has each been designated as pPM-k3 and pPM-h1, respectively, and *E. coli* having a respective plasmid has been internationally deposited under the provisions of the Budapest Treaty as NCIMB40366 and NCIMB40362 on Feb. 11, 1991 with the National Collections of Industrial and Marine Bacteria Limited.

Humanized antibody which is also called reshaped human antibody has been made by transplanting the complementarity determining regions (CDRs) of an antibody of a mammal other than the human, for example mouse antibody, into the CDRs of human antibody. The general recombinant DNA technology for preparation of such antibodies is also known (see European Patent Application EP 125023 and International Patent Application WO 92-19759).

Specifically, a DNA sequence which was designed to ligate the CDRs of mouse antibody with the framework regions (FRs) of human antibody is synthesized from several divided oligonucleotides having sections overlapping with one another at the ends thereof, and the oligonucleotides are then synthesized into one integrated DNA. The DNA thus obtained is ligated to a DNA encoding a C region of human antibody and then is integrated into an expression vector, which is introduced into a host for antibody production (see European Patent Application EP 239400 and International Patent Application WO 92-19759).

For the FRs of human antibody being ligated to CDRs, the FR that make CDR a favorable antigen-binding site is selected. When desired, Amino acids in the FR of antibody V region may be substituted so that the CDR of humanized antibody may form an appropriate antigen binding site (Sato, K. et al., Cancer Res. (1993) 53, 851-856).

A preferred embodiment of humanized antibody for use in the present invention includes humanized PM-1 antibody (see International Patent Application WO 92-19759). In the humanized PM-1 antibody, CDRs of the PM-1 antibody derived from a mouse have been ligated to the FRs of the human antibody REI for the L chain, and the FRs of the human antibody NEW, and part of the amino acid residues of the FR has been substituted to obtain antigen-binding activity.

In order to produce anti-IL-6 receptor antibody for use in the present invention, the antibody gene is integrated into an expression vector so as to be expressed under the control of an expression regulatory region, for example an enhancer and/or a promoter. Subsequently, the expression vector is transformed into a host cell and the antibody is then expressed therein.

The antibody gene may be expressed by integrating separately DNAs encoding a heavy chain (H chain) and a light chain (L chain) of an antibody into an expression vector and co-transforming the host cell, or by integrating a DNA encoding an H chain and an L chain into a single expression vector and transforming the host cell (International Patent Application WO 94-11523).

Chimeric antibody consists of the V regions of antibody derived from a mammal other than the human and the C regions derived from human antibody, whereas humanized antibody consists of the CDRs of antibody derived from a mammal other than the human and the FRs and the C regions of antibody derived from human antibody. Accordingly, since the amino acid sequences derived from a mammal other than the human are reduced to a minimum in the above antibodies, antigenicity thereof in the human body is reduced so that they are useful as the active ingredient of the therapeutic agents of the present invention.

As the C region of human antibody, there can be used, for example, $C\gamma_1$, $C\gamma_2$, $C\gamma_3$, or $C\gamma_4$. The C region of a human antibody may also be modified in order to improve the stability of antibody or of the production thereof.

5. Antibody Fragments and Modified Antibody

Antibodies for use in the present invention may be fragments of antibody or modified versions thereof as long as they bind to IL-6 receptor and thereby inhibit the binding of IL-6 and IL-6 receptor to block signal transmission and to inhibit the biological activity of IL-6. They are antibody fragments or modified antibodies which, when used in combination with a nitrogen mustard anticancer agent, have a higher therapeutic effect for myeloma than IL-6 receptor antibody alone or a nitrogen mustard anticancer agent alone.

For example, as fragments of antibody, there may be mentioned Fab, $F(ab')_2$, Fv or single-chain Fv (scFv) in which Fv's of H chain and L chain were ligated via a suitable linker. Specifically antibodies are treated with an enzyme, for example, papain or pepsin, to produce antibody fragments, or genes encoding these antibody fragments are constructed, and then integrated into an expression vector, which is expressed in a suitable host cell (see, for example, Co, M. S. et al., J. Immunol. (1994) 152, 2968-2976; Better, M. and Horwitz, A.H., Methods Enzymol. (1989) 178, 476-496; Plucktrun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

scFv can be obtained by ligating a V region of an H chain and a V region of an L chain of an antibody. In the scFv, the V region of H chain, and the V region of L chain are preferably ligated via a linker, preferably a peptide linker (Huston, J. S. et al., Proc. Natl. Acad. Sci. U.S.A. (1988) 85, 5879-5883). The V region of H chain and the V region of L chain in the scFv may be derived from any of the above-mentioned antibodies. As the peptide linker for ligating the V regions, any single-chain peptide comprising, for example, 12-19 amino acid residues may be used.

DNA encoding scFv can be obtained using a DNA encoding an H chain or a V region of an H chain of the above antibody and a DNA encoding an L chain or a V region of an L chain of the above antibody as the template by amplifying the portion of the DNA encoding the desired amino acid sequence among the above sequences by the PCR technique with the primer pair specifying the both ends thereof, and by further amplifying the combination of DNA encoding the peptide linker portion and the primer pair which defines that both ends of said DNA be ligated to the H chain and the L chain, respectively.

Once DNAs encoding scFv are constructed, an expression vector containing them and a host transformed with said expression vector can be obtained by the conventional methods, and scFv can be obtained using the resultant host by the conventional methods.

Antibody fragments may be those antibody fragments part of which sequence has undergone mutation, substitution, deletion, or insertion. These antibody fragments can be produced by obtaining the gene thereof in a similar manner to that mentioned above and by allowing it to be expressed in a host. "Antibody" as used in the claim of the present application encompasses these antibody fragments.

As modified antibodies, anti-IL-6 receptor antibody associated with various molecules such as polyethylene glycol (PEG) can be used. "Antibody" as used in the claim of the present application encompasses these modified antibodies. These modified antibodies can be obtained by chemically modifying the antibodies thus obtained. These methods have already been established in the art.

6. Expression and Production of Recombinant Antibody, Altered Antibody, and Antibody Fragment Antibody genes constructed as mentioned above may be expressed and obtained in a known manner. In the case of mammalian cells, expression may be accomplished using an expression vector containing a commonly used useful promoter, an antibody gene to be expressed, and DNA in which the poly A signal has been operably linked at 3' downstream thereof. Examples of the promoter/enhancer include human cytomegalovirus immediate early promoter/enhancer.

Additionally, as the promoter/enhancer which can be used for expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan, R. C. et al. (Nature (1979) 277, 108-114) when SV40 promoter/enhancer is used, and by the method of Mizushima, S. et al. (Nucleic Acids Res. (1990) 18, 5322) when HEF1α promoter/enhancer is used.

In the case of E. coli, expression may be conducted by operably linking a commonly used promoter, a signal sequence for antibody secretion, and an antibody gene to be expressed, followed by expression thereof. As the promoter, for example, there can be mentioned lacz promoter and araB promoter. The method of Ward, E. S. et al. (Nature (1989) 341, 544-546; FASEB J. (1992) 6, 2422-2427) may be used when lacz promoter is used, and the method of Better, M. et al. (Science (1988) 240, 1041-1043) may be used when araB promoter is used.

As a signal sequence for antibody secretion, when produced in the periplasm of E. coli, the pelB signal sequence (Lei, S. P. et al., J. Bacteriol. (1987) 169, 4379-4383) can be used. After separating the antibody produced in the periplasm, the structure of the antibody is appropriately refolded before use (see, for example, International Patent Application WO 96-30394).

As the origin of replication, there can be used those derived from SV40, polyoma virus, adenovirus, bovine papilloma virus (BPV), and the like. Furthermore, for gene amplification in the host cell system, expression vectors can include as selection markers the aminoglycoside transferase (APH) gene, the thymidine kinase (TK) gene, E. coli xanthine guaninephosphoribosyl transferase (Ecogpt) gene, the dihydrofolate reductase (dhfr) gene, and the like.

For the production of antibody for use in the present invention, any production system can be used, and the production system of antibody preparation comprises the in vitro or the in vivo production system.

As the in vitro production system, there can be mentioned a production system which employs eukaryotic cells and the production system which employs prokaryotic cells.

When eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as *Xenopus* oocytes, or (3) insect cells such as sf9, sf21, and Tn5. Known plant cells include, for example, those derived from the Nicotiana family, more specifically cells derived from *Nicotiana tabacum* which is subjected to callus culture. Known fungal cells include (1) yeasts such as the Saccharomyces family, more specifically *Saccharomyces cereviceae*, or (2) mold fungi such as the genus *Aspergillus*, more specifically *Aspergillus niger*.

When prokaryotic cells are used, there are the production systems which employ bacterial cells. Known bacterial cells include *Escherichia coli*, and *Bacillus subtilis*.

By introducing via transformation the gene of the desired antibody into these cells and culturing the transformed cells in vitro, the antibody can be obtained. Culturing is conducted in the known methods. For example, as the culture liquid for mammalian cells, DMEM, MEM, RPMI1640, IMDM and the like can be used, and serum supplements such as fetal calf serum (FCS) may be used in combination. In addition, antibodies may be produced in vivo by implanting cells into which the antibody gene has been introduced into the peritoneal cavity of an animal, and the like.

As in vivo production systems, there can be mentioned those which employ animals and those which employ plants. When animals are used, there are the production systems which employ mammals and insects.

As mammals, goats, pigs, sheep, mice, and cattle can be used (Glaster, V., SPECTRUM Biotechnology Applications, 1993).

When mammals are used, transgenic animals can be used. For-example, antibody genes are inserted into the gene encoding protein which is inherently produced in the milk such as goat A casein to prepare fusion genes. DNA fragments containing the fusion gene into which the antibody gene has been inserted are injected to a goat embryo, and the embryo is introduced into a female goat. The desired antibody is obtained from the milk produced by the transgenic goat borne to the goat who received the embryo or offsprings thereof. In order to increase the amount of milk produced containing the desired antibody produced by the transgenic goat, hormones may be given to the transgenic goat as appropriate. (Ebert, K. M. et al., Bio/Technology (1994) 12, 699-702).

Also as insects, silkworms can be used. When silkworms are used, baculovirus into which the desired antibody gene has been inserted is infected to the silkworm, and the desired antibody can be obtained from the body fluid of the silkworm (Maeda, S. et al., Nature (1985) 315, 592-594).

Moreover, when plants are used, tabacco, for example, may be used. When tabacco is used, the desired antibody gene is inserted into an expression vector for plants, for example pMON 530, and then the vector is introduced into a bacterium such as *Agrobacterium tumefaciens*. The bacterium is then infected to tobacco such as *Nicotiana tabacum* to obtain the desired antibody from the leaves of the tobacco (Ma, J. K. et al., Eur. J. Immunol. (1994) 24, 131-138).

An antibody gene is introduced, as mentioned above, into these animals or plants, and then the antibody is produced in such animals and plants and is collected therefrom.

When antibody is produced in in vitro or in vivo production systems, as mentioned above, DNAs encoding an H chain and an L chain of an antibody are separately integrated into expression vectors and the hosts are transformed simultaneously, or a DNA encoding an H chain and an L chain of an antibody is integrated into a single expression vector and the host is transformed therewith (International Patent Application WO 94-11523).

7. Separation and Purification of Antibody

Antibodies expressed and produced as described above can be separated from inside or outside of the host cell and then may be purified to homogeneity. Separation and purification of antibody for use in the present invention may be accomplished by methods of separation and purification conventionally used for proteins without any limitation.

For example, separation and purification of antibody may be accomplished by combining, as appropriate, column chromatography such as affinity chromatography, filtration, ultracentrifugation, salting-out, dialysis and the like (Antibodies: A Laboratory Manual, Ed Harlow and David Lane, Cold Spring Harbor Laboratory, 1988).

As the column used for affinity chromatography, there can be mentioned Protein A column and Protein G column. Examples of the column employing Protein A column are Hyper D, POROS, Sepharose F.F. (Pharmacia) and the like.

Chromatography other than affinity chromatography includes, for example, ion exchange chromatography, hydrophobic chromatography, gel-filtration, reverse-phase chromatography, absorption chromatography and the like (Strategies for Protein Purification and Characterization: A Laboratory Course Manual, Ed Daniel R. Marshak et al., Cold Spring Harbor Laboratory Press, 1996). Furthermore, said chromatography may be carried out using a liquid-phase chromatography such as HPLC, FPLC, and the like.

8. Measurement of Antibody Concentration

The concentration of antibody obtained as above can be determined by measurement of absorbance or by the enzyme-linked immunosorbent assay (ELISA) and the like. Thus, when absorbance measurement is employed, the antibody obtained is appropriately diluted with PBS and then the absorbance is measured at 280 nm, followed by calculation using the absorption coefficient of, though different with species and subclasses, 1.4 OD at 1 mg/ml in the case of human antibody.

When the ELISA method is used, measurement is conducted as follows. Thus, 100 µl of goat anti-human IgG antibody diluted to 1 µg/ml in 0.1 M bicarbonate buffer, pH 9.6, is added to a 96-well plate (Nunc), and is incubated overnight at 4° C. to immobilize the antibody. After blocking, 100 µl each of appropriately diluted antibody of the present invention or samples containing the antibody, or 100 µl of human IgG of a known concentration as the concentration standard is added, and incubated at room temperature for 1 hour.

After washing, 100 µl of 5000-fold diluted alkaline phosphatase-labeled anti-human IgG antibody is added, and incubated at room temperature for 1 hour. After washing, the substrate solution is added and incubated, followed by measurement of absorbance at 405 nm using the MICROPLATE READER Model 3550 (Bio-Rad) to calculate the concentration of the desired antibody based on the absorbance of the concentration standard IgG.

For determination of antibody concentration, BIAcore (Pharmacia) can be used.

9. Confirmation of the Activity of Antibody

Evaluation of activity of anti-IL-6 receptor antibody of the present invention can be conducted using a commonly known method. IL-6 is added to a plate in which IL-6 responsive cells such as HN60.BSF2 cells were cultured. Then, evaluation is made in the presence of anti-IL-6 receptor antibody, using the incorporation of $^3$H labeled thymidine by IL-6 dependent cells as an index.

Alternatively, $^{125}$I-labeled IL-6 and anti-IL-6 receptor antibody are added to a plate in which IL-6 receptor-expressing cells such as U266 have been cultured and then the amount of $^{125}$I-labeled IL-6 that is bound to the IL-6-expressing cells is determined for evaluation (Antibodies: A Laboratory Manual. Ed Harlow and David Lane, Cold Spring Harbor Laboratory, 1988).

As methods for determining the antigen-binding activity of anti-IL-6 receptor antibody for use in the present invention, there can be used ELISA, EIA (enzymeimmunoassay), RIA (radioimmunoassay), or the fluorescent antibody method.

When ELISA is employed, for example, IL-6 receptor is added to a 96-well plate onto which antibody against IL-6 receptor has been immobilized, and then samples containing the desired anti-IL-6 receptor antibody, for example a culture supernatant of anti-IL-6 receptor antibody-producing cells or purified antibody, are added thereto. Secondary antibody that recognizes the desired anti-IL-6 receptor antibody, labeled with an enzyme such as alkaline phosphatase is added, and the plate is incubated, washed, and then the enzyme substrate such as p-nitrophenyl phosphate is added thereto. Then the absorbance is measured to evaluate the antigen-binding activity. A soluble IL-6 receptor may be used as the IL-6 receptor.

As methods for measuring the inhibition activity of ligand receptor binding of the anti-IL-6 receptor antibody for use in the present invention, the conventional Cell ELISA or the ligand receptor binding assay can be used.

In the case of Cell ELISA, for example, cells expressing IL-6 receptor are cultured in a 96-well plate and then immobilized with paraformaldehyde etc. Alternatively, membrane fractions of cells expressing IL-6 receptor are prepared and a 96-well plate on which IL-6 receptors have been immobilized is prepared. To this are added a sample containing the desired anti-IL-6 receptor antibody, for example a culture supernatant of anti-IL-6 receptor antibody-producing cells, and purified antibody, and IL-6 labeled with a radioisotope such as $^{125}$I, and then the plate is incubated, washed, and radioactivity is measured to determine the amount of IL-6 bound to the IL-6 receptor and thereby to evaluate the inhibition activity of ligand receptor binding of anti-IL-6 receptor antibody.

In the inhibition assay of IL-6 binding to IL-6 receptor on the cells, cells expressing IL-6 receptors are separated by means of centrifugation etc. and resuspended to prepare a cell suspension. A solution of IL-6 labeled with a radioisotope such as $^{125}$I, or a mixture of unlabeled IL-6 and labeled IL-6, and a solution containing anti-IL-6 receptor antibody whose concentration has been adjusted are added to the cell suspension. After incubating for a certain period of time, the cells are separated, and the radioactivity of the labeled IL-6 bound to the cell is measured.

For evaluation of activity of the above antibody, BIAcore (Pharmacia) can be used.

10. Method of Administration and Pharmaceutical Preparation

In accordance with the present invention, a nitrogen mustard anticancer agent and anti-IL-6 receptor antibody are used in combination. "Used in combination" as used herein refers to a case in which pharmaceutical compositions are administered at different times, a case in which pharmaceutical compositions are administered at the same time, and a case in which one pharmaceutical composition comprising both of a nitrogen mustard anticancer agent and anti-IL-6 receptor antibody is administered. In the former two cases, a pharmaceutical composition comprising a nitrogen mustard anticancer agent and a pharmaceutical composition comprising anti-IL-6 receptor antibody may be given through the same administration route, or a different administration route. Each of these pharmaceutical compositions is given to cure or inhibit at least partially the pathological symptoms of patients suffering from diseases. The period of administration may be chosen, as appropriate, depending on the age and conditions of the patient.

Preferably, pharmaceutical compositions comprising anti-IL-6 receptor antibody may be administered parenterally, for example via intravenous injection, drip infusion, intramuscular injection, intraperitoneal injection, subcutaneous injection, and the like, either systemically or locally. As local dosage forms, preferably, external preparations, local injections, and the like are used. External preparations are chosen from liniments such as ointments, gel, cream, emulsions, and liquids, tapes, plaster tapes such as patches, or nebulas such as sprays and powders.

The effective dosage of anti-IL-6 receptor antibody is chosen from the range of 0.001 mg to 1000 Mg per kg of body weight per day. Preferably, the dosage is selected from the range of 0.01 to 50 mg per body weight. The above doses depend on the pathological conditions, and hence they are not limited to these values. The number of administration is usually selected from, but not limited to, once or twice per day, once per two to a few days, or once per one to four weeks.

Pharmaceutical compositions comprising a nitrogen mustard anticancer agent are preferably administered orally, but depending on the nature of the active ingredient, the conditions of patients, and the like, they may be given parenterally as well. For example intravenous injection, drip infusion, intraarterial injection, intramuscular injection, intratumor injection, intrathoracic injection, or intraperitoneal injection, either systemically or locally.

The effective dosage of nitrogen mustard anticancer agents is different on their kind, but for melphalan, for example, oral administration of 1 to 20 mg per day, every day or 1 to 6 times per week, or as high-dose intravenous injection or infusion, single or multiple doses of 20 to 200 mg/m$^2$ is employed. For cyclophosphamide, oral or intravenous administration of 50 to 2000 mg per dose usually for one to 5 times per week, to once per two weeks to one month is employed. The number and the schedule of administration are not limited to those mentioned above. Nitrogen mustard anticancer agents may be given not only alone but also in combination with vincristine, adriamycin, prednisolone, and the like, as appropriate.

When a pharmaceutical composition comprising a nitrogen mustard anticancer agent is administered simultaneously with anti-IL-6 receptor antibody, the ratio, is, when combined with daily oral administration of melphalan, 0.01 to 1000 fold (weight ratio) relative to the dose of melphalan, though it is different on the conditions of the patient and the administration schedule. Alternatively a pharmaceutical composition comprising a certain ratio of the two agents may be administered. However, as mentioned above, the dose ratio varies with the conditions of the patient etc., and hence it is not limited to the ratio mentioned above.

It is also possible to set up a schedule in which a pharmaceutical composition comprising a nitrogen mustard anticancer agent and anti-IL-6 receptor antibody are given at different time points. For example, to patients for whom remission was introduced by applying a nitrogen mustard anticancer agent or a combined therapy including the agent as a constituent element, anti-IL-6 receptor antibody can be administered in order to maintain remission. Furthermore, administration of a nitrogen mustard anticancer agent or a combined therapy having the agent as a constituent element and administration of anti-IL-6 receptor antibody may be repeated every 1 to 4 weeks. For a nitrogen mustard anticancer agent and anti-IL-6 receptor antibody, preferably the former is given first, but the latter may be given first depending on the conditions of the patient etc.

Pharmaceutical compositions of the present invention comprising nitrogen mustard anticancer agents, pharmaceutical compositions comprising anti-IL-6 receptor antibody, and pharmaceutical compositions comprising a nitrogen mustard anticancer agent and anti-IL-6 receptor antibody of the present invention may contain pharmaceutically acceptable carriers and/or additives depending on the route of administration.

Examples of such carriers or pharmaceutical additives include water, a pharmaceutically acceptable organic solvent, collagen, polyvinyl alcohol, polyvinylpyrrolidone, a carboxyvinyl polymer, sodium carboxymethylcellulose, sodium, polyacrylate sodium alginate, water-soluble dextran, sodium carboxymethyl starch, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, pharmaceutically acceptable surfactants and the like.

Actual additives are chosen from, but not limited to, the above or combinations thereof depending on the dosage form of a therapeutic agent of the present invention.

The present invention also encompasses a simultaneous or sequential combined administration of a pharmaceutical agent of the present invention with another agent, a biological agent, or a synthetic agent. Other agents are selected from anti-inflammatory agents, antiallergic agents, anti-platelet agents, other anticancer agents or those that enhance or supplement the activity of the object of the present invention.

EXAMPLES

The present invention will now be explained hereinbelow in more detail with reference to the following reference examples, experimental examples and working examples. It is to be noted that the present invention is not limited to these examples in any way.

Reference Example 1

Construction of the Anti-IL-6 Receptor Antibody PM-1

The anti-IL-6 receptor antibody MT18 prepared by the method of Hirata et al. (J. Immunol. (1989) 143, 2000-2006) was bound to CNBr-activated Sepharose 4B (manufactured by Pharmacia Fine Chemicals, Piscataway, N.J.) in accordance with the attached directions to purify IL-6 receptor (Yamasaki et al., Science (1988) 241, 825-828).

Thus, a human myeloma cell line U266 was solubilized in 1 mM p-paraminophenylmethane sulphonylfluoride hydrochloride (manufactured by Wako Chemicals) (digitonin buffer) containing 1% digitonin (manufactured by Wako Chemicals), 10 mM triethanolamine (pH 7.8), and 0.15 M NaCl, and then mixed with MT18 antibody conjugated to Sepharose 4B beads. The beads were then washed six times with the digitonin buffer to prepare partially purified IL-6 receptor to be used for immunization.

BALB/c mice were immunized four times every 10 days with the above-mentioned partially purified IL-6 receptor obtained from $3\times10^9$U266 cells, and then hybridomas were prepared in a conventional method. A culture supernatant of hybridomas from growth-positive wells was evaluated for its ability of binding to IL-6 receptor by the method described below. $5\times10^7$U266 cells were labeled with $^{35}$S-methionine (2.5 mCi) and were solubilized in the above digitonin buffer.

The solubilized U266 cells were mixed with 0.04 ml of MT18 antibody conjugated to Sepharose 4B beads and then washed six times in the digitonin buffer. Using 0.25 ml of the digitonin buffer (pH 3.4), $^{35}$S-methionine labeled IL-6 receptor was eluted, which was neutralized with 0.025 ml of 1 M Tris, pH 7.4. The hybridoma culture supernatant 0.05 ml was mixed with 0.01 ml Protein G Sepharose (manufactured by Pharmacia).

After washing, the Sepharose was incubated with 0.005 ml solution of $^{35}$S-labeled IL-6 receptor prepared above. Immunoprecipitating substances were analyzed by SDS-PAGE to search the culture supernatants of hybridoma that reacts with IL-6 receptor. As a result, a reaction-positive hybridoma clone PM-1 was established. The anti-IL-6 receptor antibody PM-1 produced from the hybridoma PM-1 had the IgG1 κ subtype.

The activity of the antibody produced by the hybridoma PM-1 to inhibit the binding of IL-6 to IL-6 receptor was evaluated using a human myeloma cell line U266. Recombinant human IL-6 was prepared from *E. coli* (Hirano et al., Immunol. Lett. (1988) 17, 41), and was labeled with $^{125}$I using the Bolton-Hunter reagent (New England Nclear, Boston, Mass.) (Taga et al., J. Exp. Med. (1987) 166, 967).

$4\times10^5$ U266 cells were cultured with a culture supernatant of 70% (v/v) hybridoma PM-1 and 14000 CPM of $^{125}$I-labeled IL-6 at room temperature for one hour in the presence of a 100-fold excess of non-labeled IL-6. Seventy microliters of a sample was layered onto 300 μl of FCS in a 400 μl microfuge polyethylene tube, centrifuged, and then the radioactivity of the cells was measured. The result revealed that the antibody produced by the hybridoma PM-1 inhibits the binding of IL-6 to IL-6 receptor.

Reference Example 2

Construction of a Reshaped Human PM-1 Antibody

A reshaped human PM-1 antibody was obtained by the method described in International Patent Application WO 92-19759. From the hybridoma PM-1 prepared in Reference example 1, total RNA was prepared in the conventional method, from which single-stranded cDNA was synthesized. By the polymerase chain reaction (PCR) method, DNA encoding the V region of mouse PM-1 antibody was amplified. The primers used in the PCR method are those described in Jones, S. T. et al., Bio/Technology (1991) 9, 88-89, 1991.

The PCR-amplified DNA fragments were purified to obtain DNA fragments containing the gene encoding the V region of mouse kappa-type L chain and DNA fragments containing the gene encoding the V region of mouse gamma-type H chain. These DNA fragments were ligated to a plasmid pUC19, which was then transfected into competent *E. coli* cells CH$_5$α to obtain an *E. coli* transformant. From the transformant thus obtained, the above plasmid was obtained, and the base sequence of the V region-coding region in the plasmid was determined in a conventional method, and the complementarity determining region (CDR) of each V region was identified.

In order to construct vectors that express chimera PM-1 antibody, cDNAs encoding the V region of κ L chain and H chain of mouse PM-1 were separately inserted into HCMV expression vectors. In order to construct a reshaped human PM-1 antibody, the CDR of V region of mouse PM-1 was implanted to human antibody by the CDR grafting method. In order for the CDR of human antibody to form appropriate antigen-binding sites, substitution of amino acids of the framework region (FR) of antibody V region was conducted.

In order to express genes of L chain and H chain of the reshaped human PM-1 antibody thus constructed, DNA encoding the L chain or the H chain was separately inserted into a vector containing the human elongation factor 1α (HEF-1α) promoter, and a vector expressing the L chain or the H chain of the reshaped human PM-1 (hPM-1) antibody was constructed. By simultaneously inserting these two expression vectors into CHO cells, a cell line that produces reshaped human PM-1 antibody (hPM-1) was established. The ability of hPM-1 thus obtained to bind to human IL-6 receptor was confirmed by ELISA. Furthermore, hPM-1 inhibited the binding of human IL-6 to human IL-6 receptor in a similar manner to that of mouse antibody and chimeric antibody.

Example 1

The Effects of Combined Use of Anti-Human IL-6 Receptor Antibody and a Chemotherapeutic Agent on the Growth of Human Myeloma Cells The effects of anti-human IL-6 receptor antibody on sensitivity of KPMM2 cells to chemotherapeutic agents used for treatment of myeloma such as adriamycin (ADR, manufactured by Kyowa Hakko), vincristine (VCR, manufactured by Sigma Chemical Co.), and melphalan (L-PAM, manufactured by Sigma Chemical Co.) were evaluated.

KPMM2 is a multiple myeloma cell line derived from the ascites of a human patient with myeloma (see Japanese Unexamined Patent Publication (Kokai) No. 7-236475). The patient with myeloma had maintained remission by the MCNU (ranimustine) and MP (melphalan, prednisolone) therapy, but the disease recurred and the subsequent VAD (vincristine, adriamycin, dexamethasone) therapy was ineffective. The growth of KPMM2 cells is promoted by IL-6 and is markedly inhibited by anti-IL-6 antibody or anti-IL-6 receptor antibody (Rinsho Ketueki [The Japanese Journal of Clinical Hematology] (1994) 35, 1361-1365). The growth activity of the cell was evaluated by incorporation of $^3$H-labeled thymidine (manufactured by Amersham) into the cell.

The KPMM2 cells that had been maintained were washed thoroughly with a fresh medium (RPMI1640 medium supplemented with 20% FBS), and then were adjusted to $4\times10^5$/ml, which was dispensed in 50 μl aliquots in a 96-well flat-bottomed microtiter plate (manufactured by Falcon). Furthermore, a medium containing a recombinant human IL-6 (Asagoe, Y. et al., Bio/Technology (1988) 6, 806-809), anti-human IL-6 receptor antibody hPM-1 (see the above reference example 1 or International Patent Application WO 92-15759), and the above chemotherapeutic agents or a fresh medium as control were added to make 200 μl in each well.

The plate was incubated at 37° C. for 4 days under the humidified condition in the presence of 5% $CO_2$. At four hours before the end of incubation, 10 μl of $^3$H-labeled thymidine solution (100 μCi/ml) was added to each well, and then incubated for more 4 hours. At the end of incubation, the cells were collected onto the glass filter (manufactured by Printed Filtermat A, WALLAC) using a harvester (Micro 96 Harvester, manufactured by SKATRON Instruments). The radioactivity incorporated into the cells was measured by a microbeta (1450 MicroBeta, manufactured by WALLAC).

The activity of growth inhibition on KPMM2 was expressed using the effect by a chemotherapeutic agent alone as the control. Using the incorporation of $^3$H-labeled thymidine into the cell for each experimental group in which a each concentration of a chemotherapeutic agent was added as 100, the amount of $^3$H-labeled thymidine incorporated into the cell in an experimental group in which anti-human IL-6 receptor antibody was simultaneously added was compared as an index.

Figure 2:
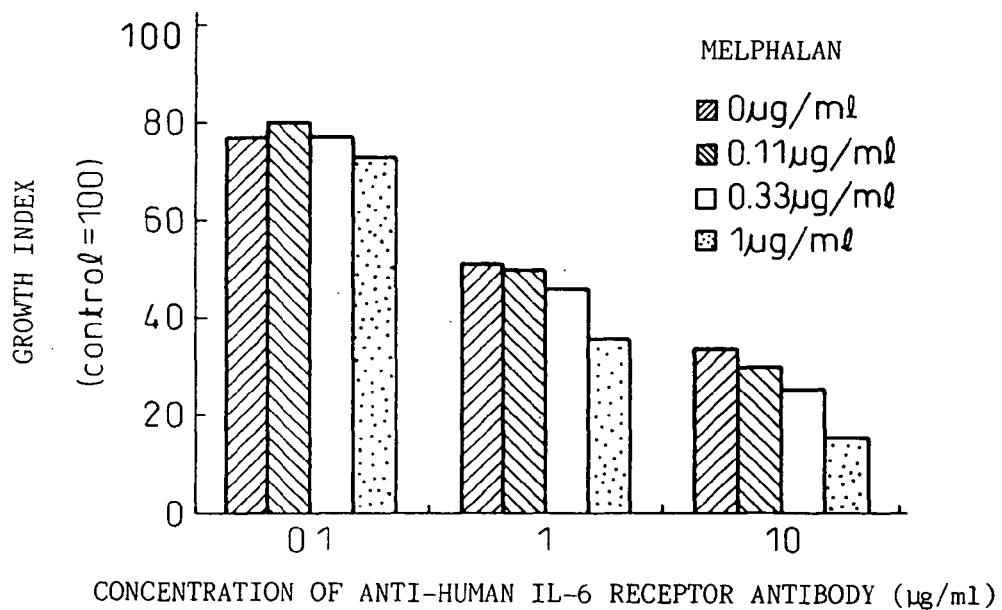
FIG. 2 is a graph showing the relationship of anti-human IL-6 receptor antibody concentration and melphalan concentration with the growth (incorporation of $^3$H-labeled thymidine) of a human myeloma cell line in the presence of 1 ng/ml IL-6.
Figure 3:
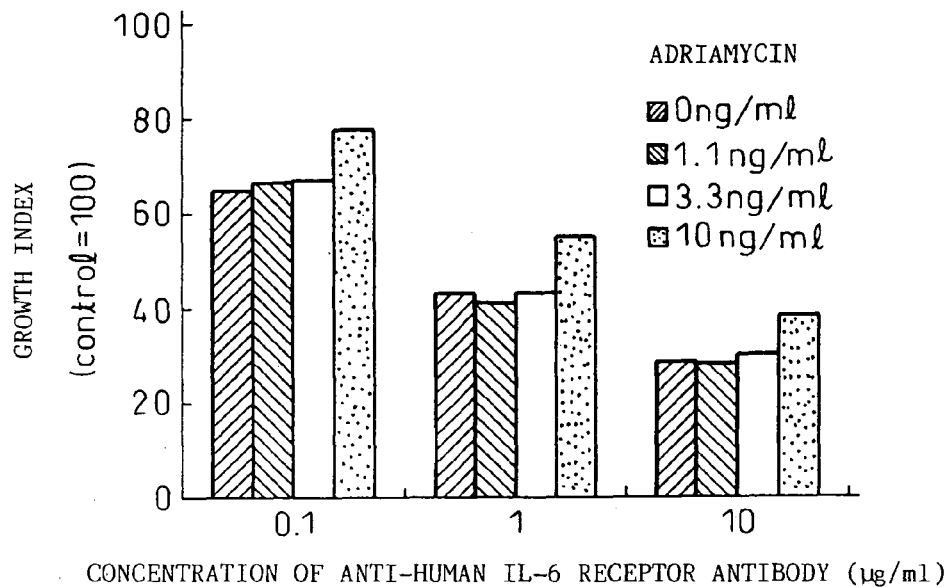
FIG. 3 is a graph showing the relationship of anti-human IL-6 receptor antibody concentration and adriamycin concentration with the growth (incorporation of $^3$H-labeled thymidine) of a human myeloma cell line in the presence of 0.1 ng/ml IL-6.
Figure 4:
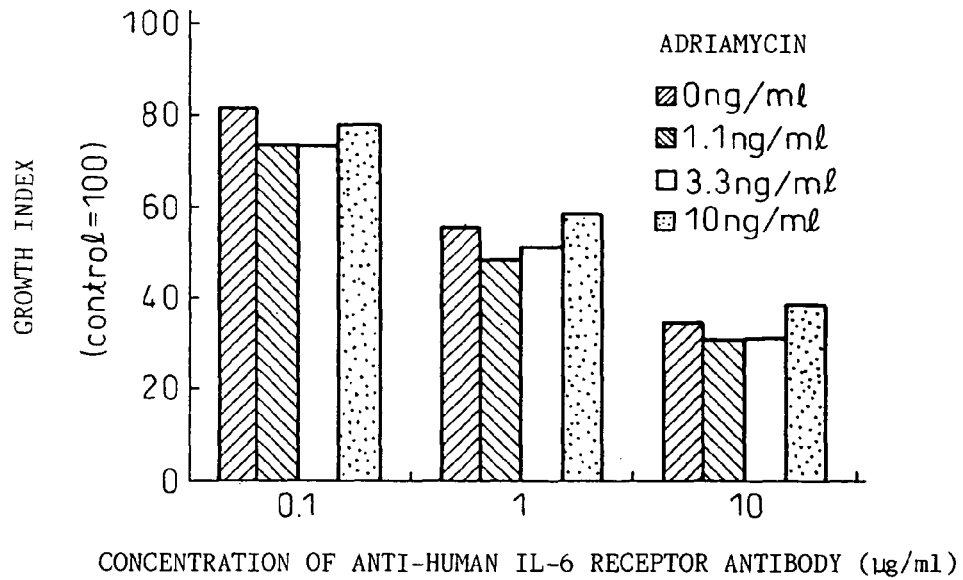
FIG. 4 is a graph showing the relationship of anti-human IL-6 receptor antibody concentration and adriamycin concentration with the growth (incorporation of $^3$H-labeled thymidine) of a human myeloma cell line in the presence of 1 ng/ml IL-6.
Figure 5:
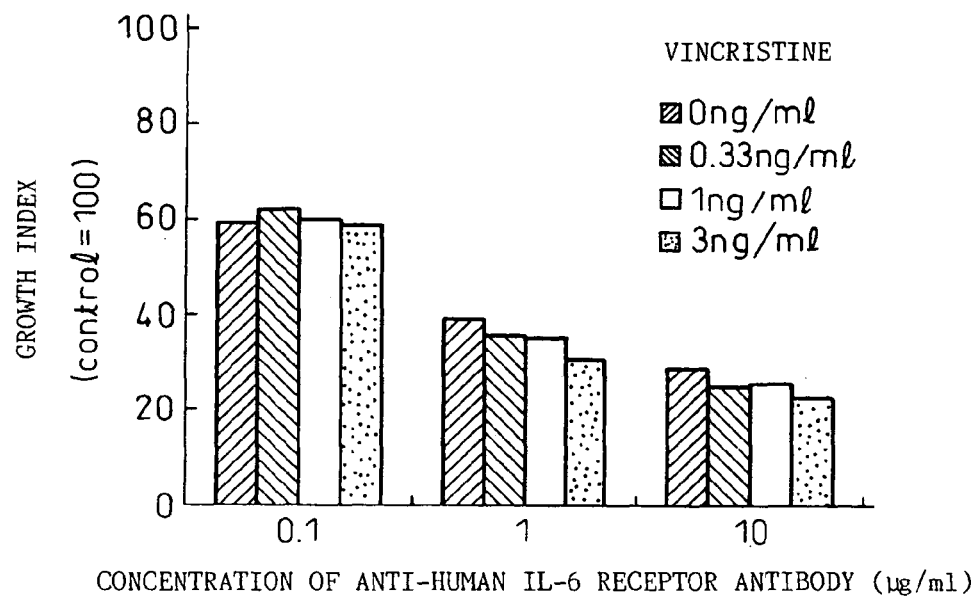
FIG. 5 is a graph showing the relationship of anti-human IL-6 receptor antibody concentration and vincristine concentration with the growth (incorporation of $^3$H-labeled thymidine) of a human myeloma cell line in the presence of 0.1 ng/ml IL-6.
Figure 6:
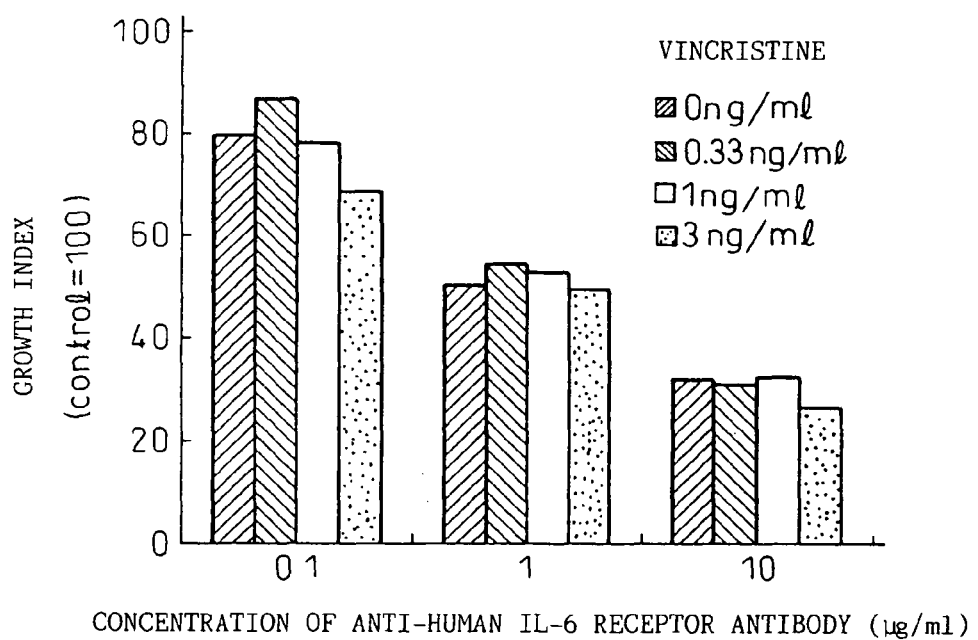
FIG. 6 is a graph showing the relationship of anti-human IL-6 receptor antibody concentration and vincristine concentration with the growth (incorporation of $^3$H-labeled thymidine) of a human myeloma cell line in the presence of 1 ng/ml IL-6.

As a result, comparison of the relationship with the concentration of a chemotherapeutic agent in the presence of a fixed concentration of anti-human IL-6 receptor antibody revealed that the index of adriamycin and vincristine was almost constant regardless of their concentration (FIG. 3 to FIG. 6), whereas the index decreased with the increase in melphalan concentration (FIG. 1 and FIG. 2). In the presence of 1 ng/ml IL-6, the growth index of 10 μg/ml anti-IL-6 receptor antibody alone was 33.9, whereas it dropped to 15.5 in the co-existence of 1 μg/ml melphalan. Similar results were obtained in the presence of 0.1 μg/ml of IL-6 and the index of the antibody alone was 28.4, whereas in the co-existence of 1 μg/ml melphalan, it was 15.9. Thus, combined use of anti-IL-6 receptor antibody and melphalan was shown to have a synergistic effect.

Example 2

The Effects of Combined Use of Anti-Human IL-6 Receptor Antibody and a Chemotherapeutic Agent in a Human Meloma Cell-Implanted SCID Mouse System It was shown in working example 1 that anti-human IL-6 receptor antibody enhances the antitumor effect of chemotherapeutic agents. Among them, melphalan (manufactured by Sigma Chemical Co.) which was found to act in a synergistic manner was used to study an in vivo effect of combined use.

For evaluation of antitumor activity, a xenograft model was used. Thus, KPMM2, a human myeloma cell line derived from ascites of a patient with multiple myeloma was implanted to a male SCID mouse (FOX CHASE C. B17/Icr-Scid Jcl, purchased from Nippon Klea) via the tail vein. At this time, the tumor cells grow in the bone marrow and come to produce myeloma protein (M protein) in the peripheral blood. Furthermore, this model system is very close to an actual clinical condition in that it develops major symptoms of multiple myeloma in humans such as bone disorders, elevated blood calcium, and the like.

Single cell suspension of myeloma cells for implantation was prepared by passing through a mesh the well minced KPMM2 cells that have been maintained in vivo. Cell density was adjusted to $3 \times 10^7$/ml, which was implanted at 0.2 ml per mouse via the tail vein ($6 \times 10^7$ cells per mouse). The day when the cells were implanted was set at day 0.

With regard to anti-human IL-6 receptor antibody, a stock solution that had been preserved at 12.1 mg/ml was diluted in sterile phosphate buffer to make 5 mg/ml. This was given to mice at 0.2 ml per animal via the tail vein on day 8 (1 mg per mouse). The control group received sterile phosphate buffer containing no antibody in a similar manner.

Melphalan (L-PAM, manufactured by Sigma Chemical Co.) that was suspended at 0.3 or 0.1 mg/ml in 0.2% CMC (carboxymethylcellulose) solution in water was used. This was given orally at 0.1 ml per 10 g body weight of mouse (3 or 1 mg/kg weight) for 0.5 consecutive days starting on day 1. The control group received 0.2% CMC solution in water containing no melphalan in a similar manner.

The experiment was carried out on the following six groups: (1) the melphalan and antibody non-administration group; (2) the 1 mg/kg melphalan single-drug administration group; (3) the 3 mg/kg melphalan single-drug administration group; (4) antibody single-drug administration group; (5) the 1 mg/kg melphalan and antibody combined administration group; and (6) the 3 mg/kg melphalan and antibody combined administration group. Group 1 included 9 mice, whereas each of the other groups included 7 mice. Furthermore, tumor was not implanted on mice of the same lineage and purchased on the same day, which were used as negative control for M protein detection.

Indices of the drug efficacy included the survival period, the survival ratio without disease on day 120, and the amount of M protein on day 30. For analysis using a survival curve, a generalized Wilcoxon's test (SPSS for windows ver. 6, SPSS inc.) was used. A significance level of 5% or lower was considered to be significant.

Serum M protein was detected as human IgG using the ELISA method. First, mouse serum was dispensed into a 96-well micro plate that had previously been coated with anti-human IgG antiserum and was allowed to stand. Then alkaline phosphatase-conjugated human IgG antibody was bound thereto, and SIGMA104 phosphatase substrate was added for color development, absorbance of which was read using a microplate reader. M protein content in the serum was calculated using the standard curve obtained from normal human IgG.

Figure 7:
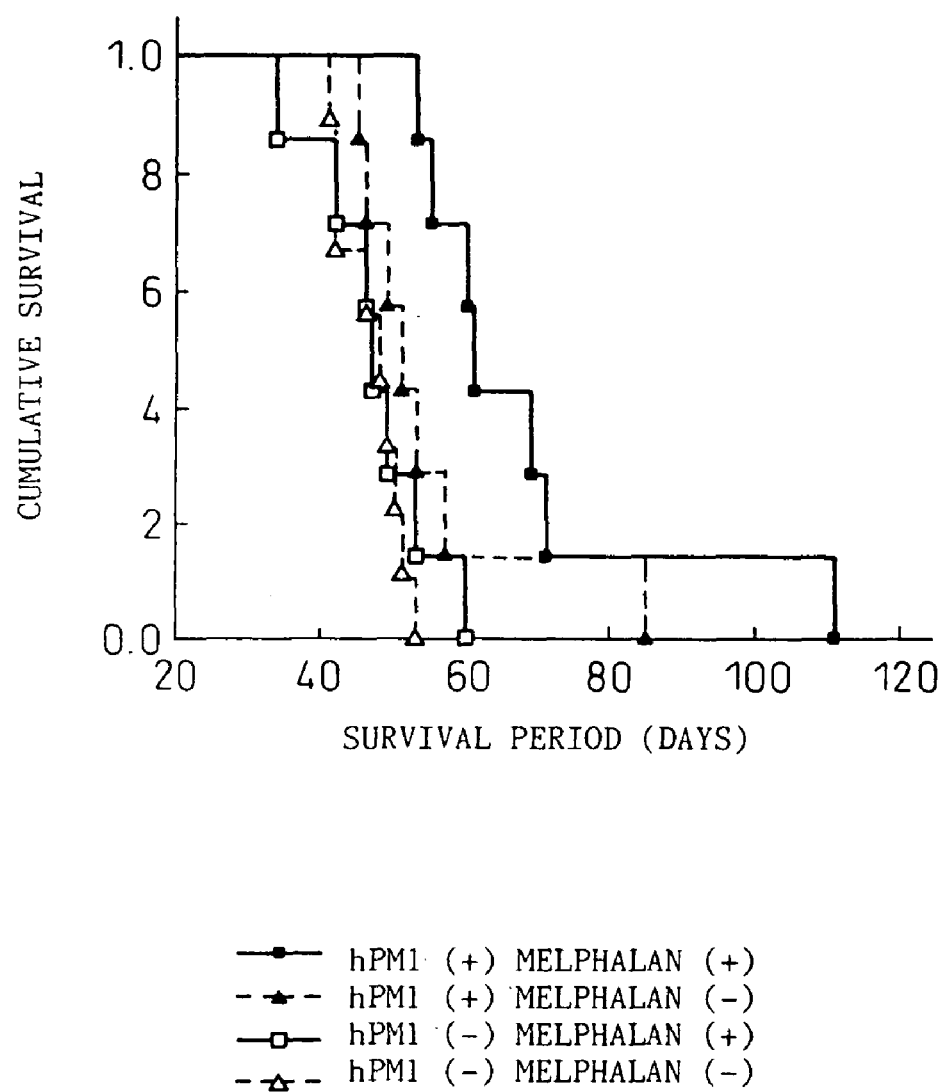
FIG. 7 is a graph showing the survival days of the mice implanted with human myeloma cells in a single-drug administration (1 mg/kg) of anti-human IL-6 receptor antibody (hPM-1) and melphalan, or in a combined use thereof.
Figure 8:
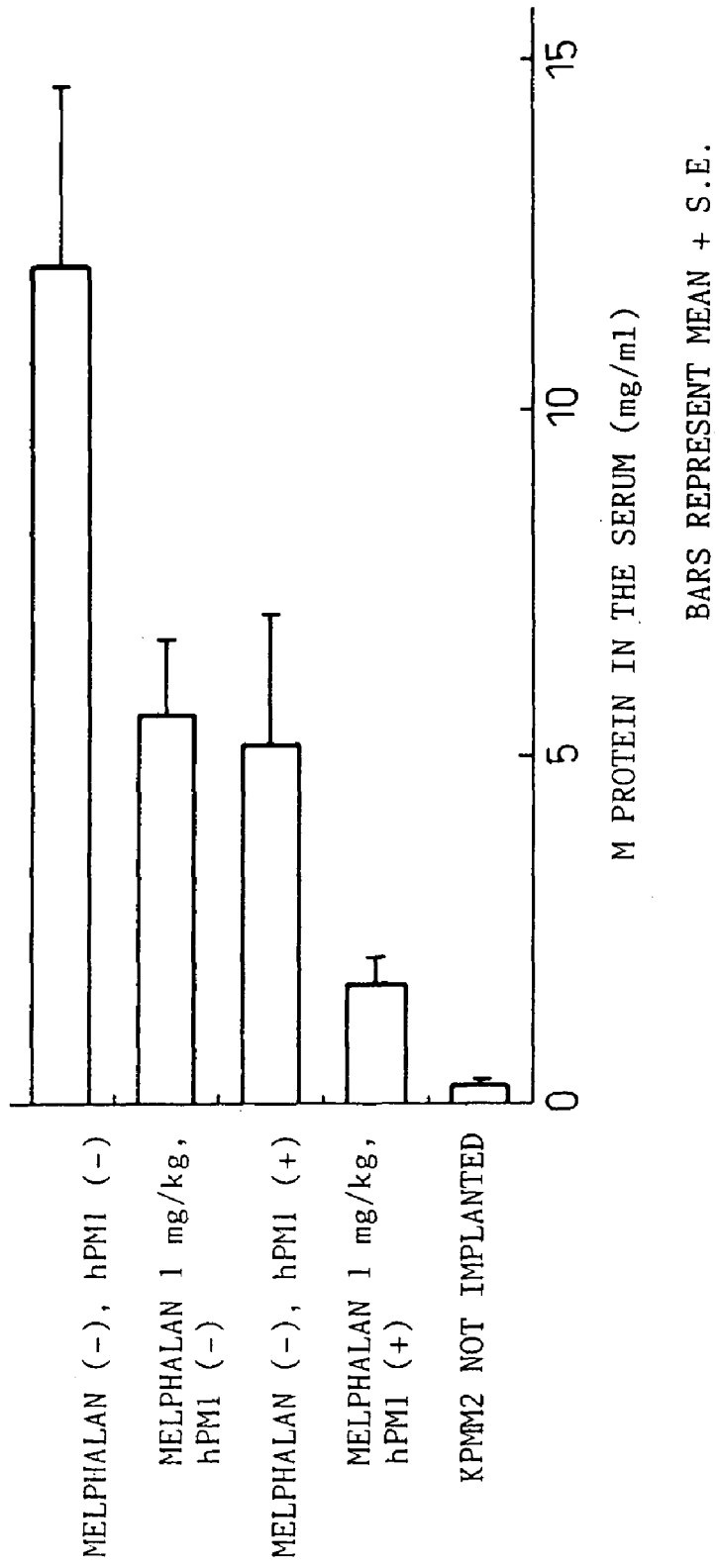
FIG. 8 is a graph showing the amount of M protein in the mice implanted with human myeloma cells in a single-drug administration (1 mg/kg) of anti-human IL-6 receptor antibody (hPM-1) and melphalan, or in a combined use thereof.
Figure 9:
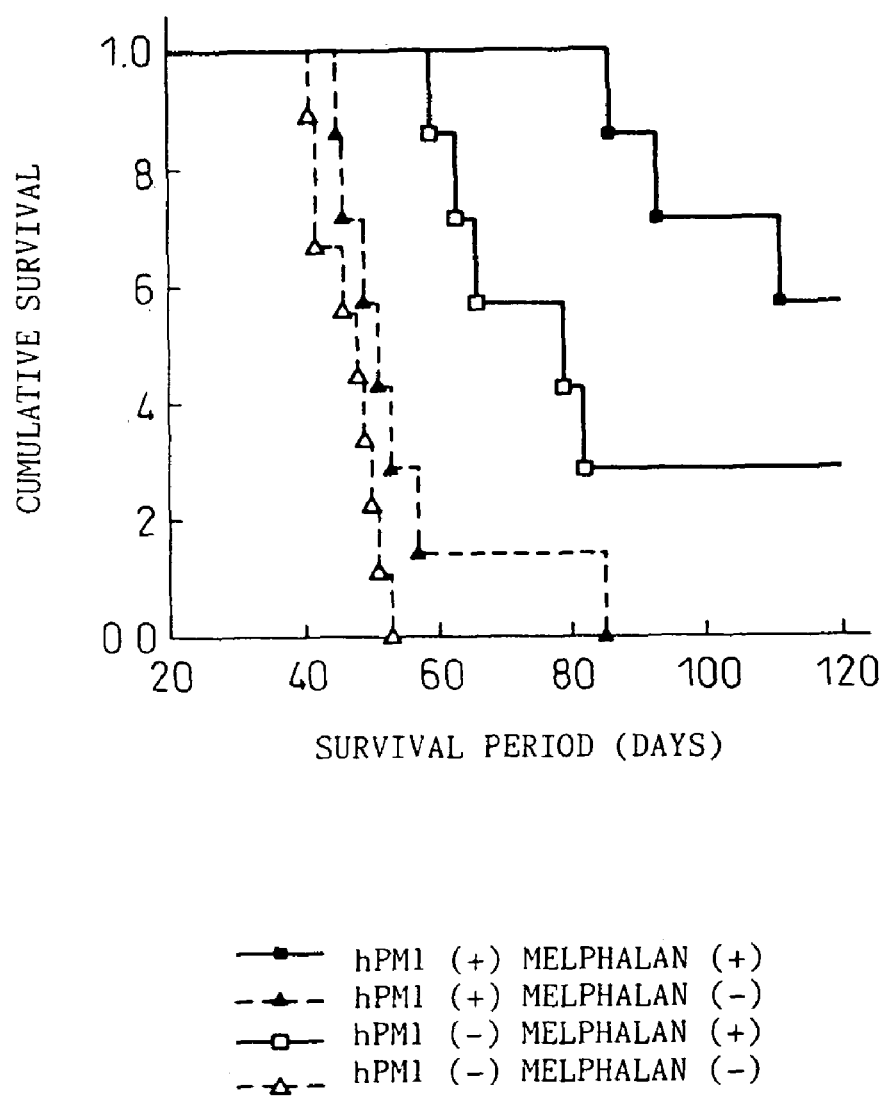
FIG. 9 is a graph showing the survival days of mice implanted with human myeloma cells in a single-drug administration (3 mg/kg) of anti-human IL-6 receptor antibody (hPM-1) and melphalan, or in a combined use thereof, with a synergistic effect obtained by the combined use.

In the anti-IL-6 receptor antibody single-drug administration group or the 1 mg/ml melphalan administration group, no life elongation effect was observed as compared to the non-administration group. But the combined use of them significantly elongated life span as compared to the non-administration group or both of the single-drug administration groups (FIG. 7). Furthermore, in the measurement of M protein in the serum on day 30 after implantation, the combined use of them reduced M protein level (FIG. 8). In the case of 3 mg/kg melphalan, a significant life elongation effect was observed for the melphalan single-drug administration group as compared to the non-administration group, but by using antibody in combination a significant life elongation effect was even observed compared to the single-drug administration (FIG. 9). The survival ratio without disease on day 120 was 2/7 in the 3 mg/kg melphalan single-drug administration group, but the ratio improved to 4/7 in the antibody combined administration group (Table 1).

Figure 10:
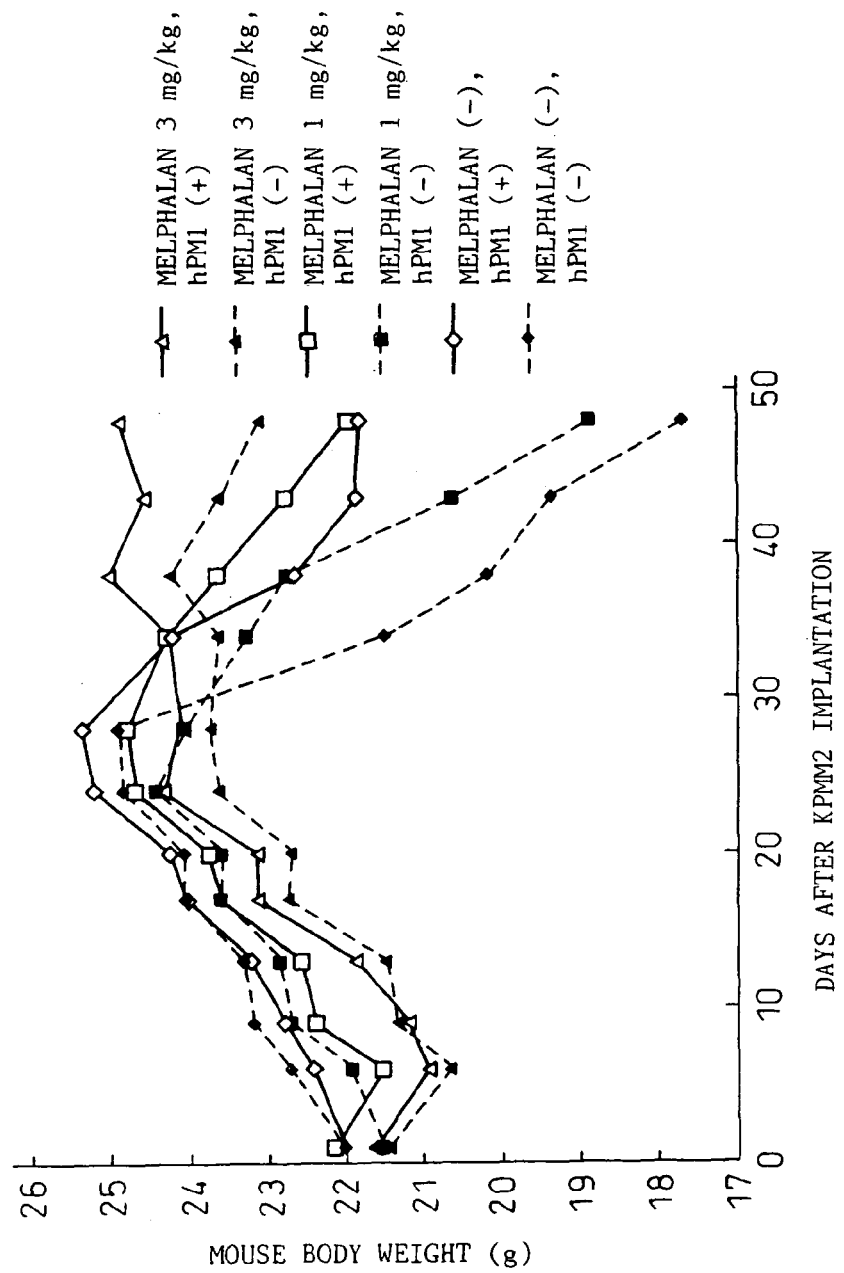
FIG. 10 is a graph showing the changes in body weight of mice implanted with human myeloma cells in a single-drug administration of anti-human IL-6 receptor antibody (hPM-1) and melphalan, or in a combined use thereof.

The administration of melphalan caused toxicity in mice and inhibited body weight gain (FIG. 10). When melphalan was used in combination with anti-IL-6 receptor antibody, an antitumor effect was enhanced but it did not expand toxicity (inhibition of body weight gain).

TABLE 1

Extension of survival period by combined use of
anti-human IL-6 receptor antibody hPM-1 and melphalan

| hPM-1 administration | Melphalan dosage | n | Survival period | Life-elongation ratio (%) | None disease ratio |
|---|---|---|---|---|---|
| — | CMC control | 9 | 46.9 ± 1.5 | 100 | 0/9 |
| — | 1 mg/kg | 7 | 47.3 ± 3.1 | 101 | 0/7 |
| — | 3 mg/kg | 7 | 84.1 ± 9.1 | 175 | 2/7 |
| day 8 | CMC control | 7 | 55.1 ± 5.2 | 118 | 0/7 |
| day 8 | 1 mg/kg | 7 | 68.6 ± 7.5 | 146 | 0/7 |
| day 8 | 3 mg/kg | 7 | 110.0 ± 5.1 | 235 | 4/7 |

Life elongation ratio *: 100×(drug administration group/drug non-administration group).

Survival period was expressed as mean±standard error.

It was revealed that by using anti-IL-6 receptor antibody and melphalan in combination, the life elongation effect was significantly enhanced in KPMM2 which is a cell line derived from a patient who was resistant to MP and VAD therapy.

Example 3

The Effects of Combined Use of Anti-Human IL-6 Receptor Antibody and a Chemotherapeutic Agent in a Human Myeloma Cell-Implanted SCID Mouse System—a Study on In Vivo Dose Dependency of Antibody Example 2 has shown that anti-human IL-6 receptor antibody enhances the antitumor effect of melphalan. Accordingly, we studied dose dependency of anti-human IL-6 receptor antibody in the combined administration of anti-human IL-6 receptor antibody and melphalan.

For evaluation of antitumor effects, a xenograft model animal that was produced by implanting KPMM2 cells via the tail vein was used as in Working example 2. Thus, single-cell suspensions which were prepared by passing through a mesh KPMM2 cells that were minced after having been maintained in vivo were implanted at 0.2 ml per, mouse via the tail vein ($6 \times 10^6$ cells per mouse). The day when the cells were implanted was set at day 0.

With regard to anti-human IL-6 receptor antibody hPM-1, a stock solution that had been preserved at 6.57 mg/ml was diluted in sodium phosphate buffer to make each solution of 5, 1, 0.2, and 0.04 mg/ml. They were given to mice at 0.1 ml per 10 g body weight of mouse via the tail vein on day 14 to create the 50, 10, 2, and 0.4 mg/kg administration groups. The control group received the same buffer without antibody in a similar manner.

Melphalan (L-PAM, manufactured by Sigma Chemical Co.) was used as a suspension of 0.1 mg/ml in 0.2% CMC solution in water. This was given orally at 0.1 ml per 10 g body weight of mouse (1 mg/kg weight) for 5 consecutive days starting on day 7. The control group received 0.2% CMC solution in water without melphalan in a similar manner.

The experiment was carried out on the following 10 groups: (A) the melphalan and the antibody non-administration group; (B) the melphalan single-drug administration group; (C) the each dose of antibody single-drug administration group, 4 groups (50, 10, 2, 0.4 mg/kg weight); and, (D) the melphalan and the each dose of antibody combined administration group, 4 groups (50, 10, 2, 0.4 mg/kg weight). The non-administration group included 12 mice per group, the melphalan administration group 6 mice per group, whereas each of the other groups included 7 mice. Furthermore, mice of the same lineage and purchased on the same day were raised without implanting a tumor, and the animals were used as negative control for M protein detection. The amount of M protein was calculated as described in Example 2.

Indices of the drug efficacy included the survival period, and the amount of M proteins on day 30, day 35, and day 42. For analysis of the survival period, a generalized Wilcoxon's test (SPSS for Windows ver. 6, SPSS inc.) was used. A significance level of 5% or lower was considered to be significant. For analysis of the amount of M protein in the serum, the ANOVA (Analysis of variance, SPSS for windows ver. 6, SPSS inc.) was first conducted. After confirming significance, Bonferroni method (SPSS for windows ver. 6, SPSS inc.) was used, and a significance level of 5% or lower was considered to be significant.

Since death cases occurred on day 35 in the non-administration group and the each dose of antibody single-drug administration group, they were compared for the amount of M protein on day 30. On the other hand, in the melphalan single-drug administration group, and the melphalan and antibody combined administration group, the amount of M protein on day 30 was very low. Since the anti-human IL-6 receptor antibody that had been administered was detected as M protein thus affecting the assay, they were compared for the data on day 35 and day 42.

Figure 11:
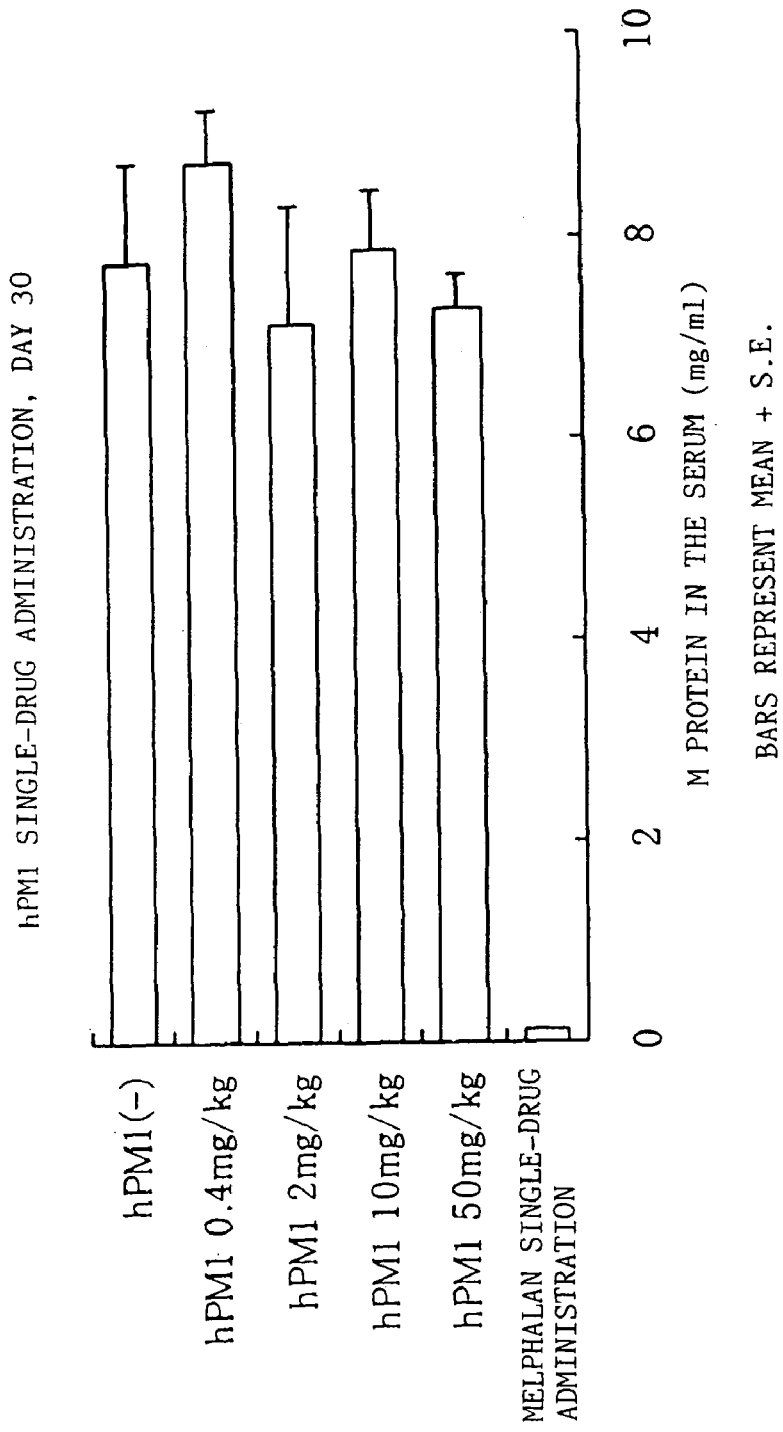
FIG. 11 is a graph showing the amount of M protein in the serum of mice implanted with human myeloma cells at 30 days after the tumor implantation in the anti-human IL-6 receptor antibody (hPM1) single-drug administration group and in the melphalan single-drug administration group.
Figure 12:
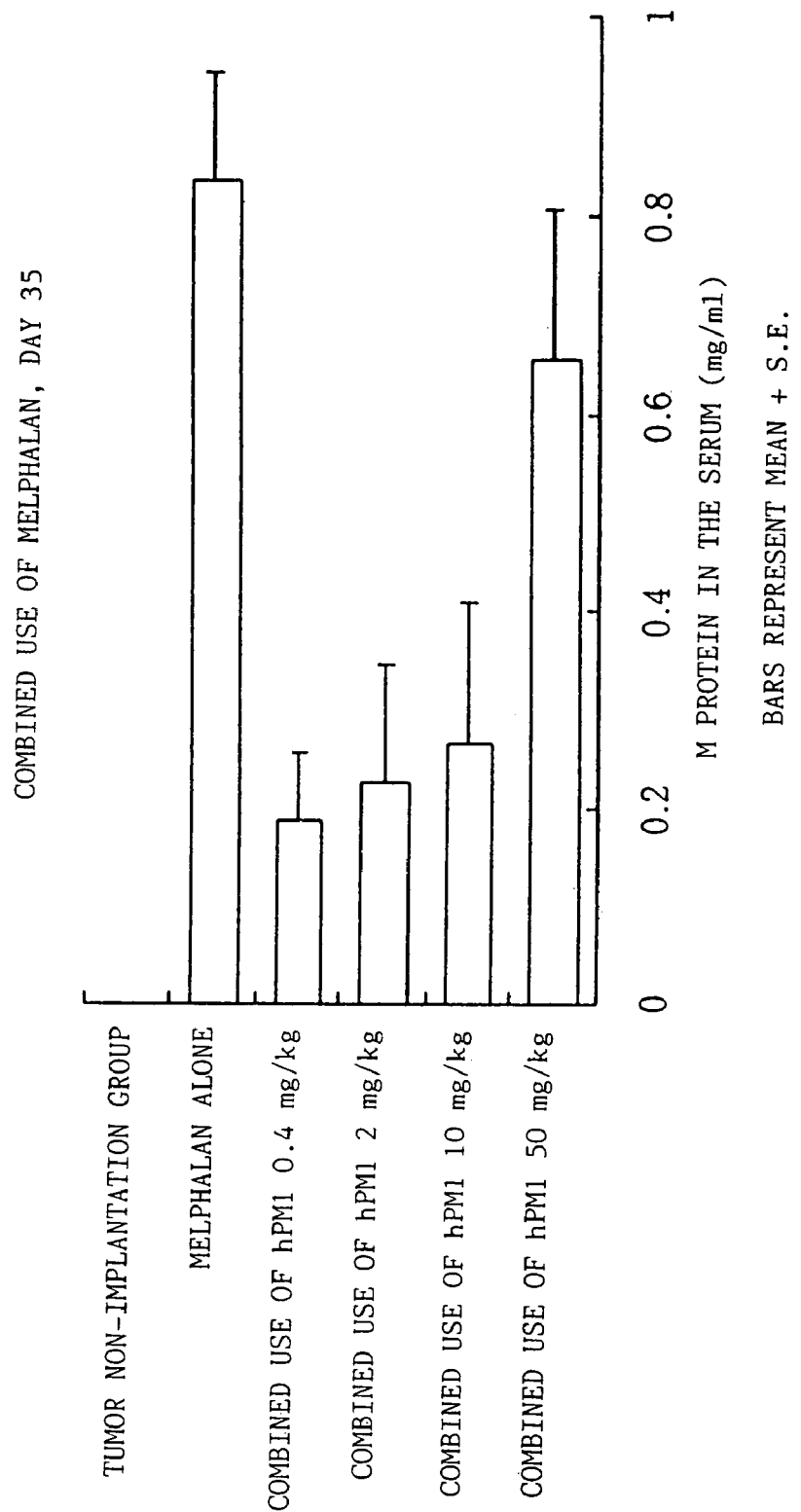
FIG. 12 is a graph showing the amount of M protein in the serum of mice implanted with human myeloma cells at 35 days after the tumor implantation in the melphalan single-drug administration group and the anti-human IL-6 receptor antibody (hPM1)-combined administration group.
Figure 13:
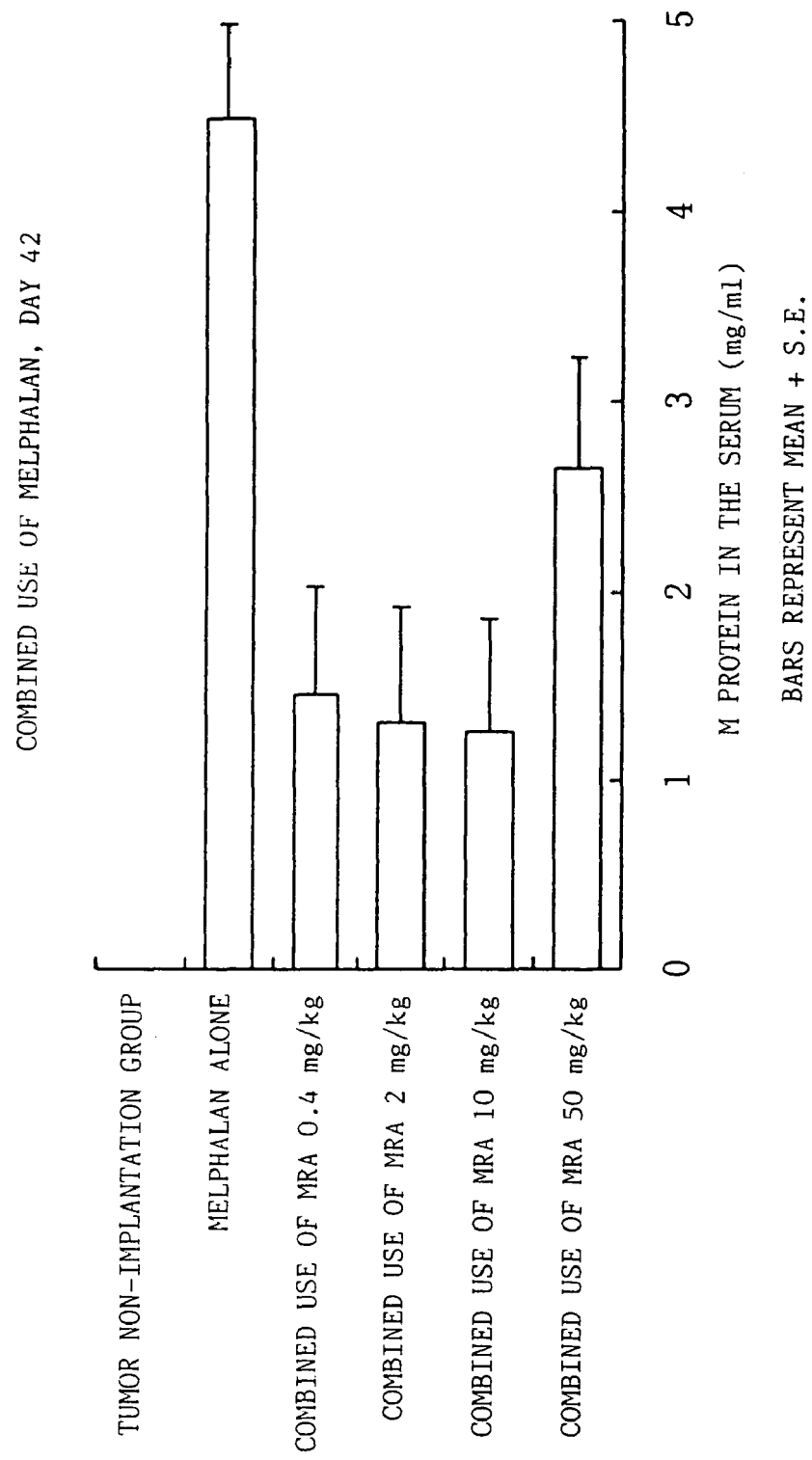
FIG. 13 is a graph showing the amount of M protein in the serum of mice implanted with human myeloma cells at 42 days after the tumor implantation in the melphalan single-drug administration group and the anti-human IL-6 receptor antibody (hPM1)-combined administration group.

On day 30 in the antibody single-drug administration group, none of the doses significantly inhibited the amount of M protein, but the single-drug administration of melphalan significantly inhibited this (FIG. 11). Then, on day 35 and 42, the effect of combined use of antibody administration relative to the melphalan administration was studied. The result revealed that the combined use of anti-human IL-6 receptor antibody at 10 mg/kg, 2 mg/kg, and 0.4 mg/kg significantly reduced the amount of M protein (FIG. 12, 13).

Figure 14:
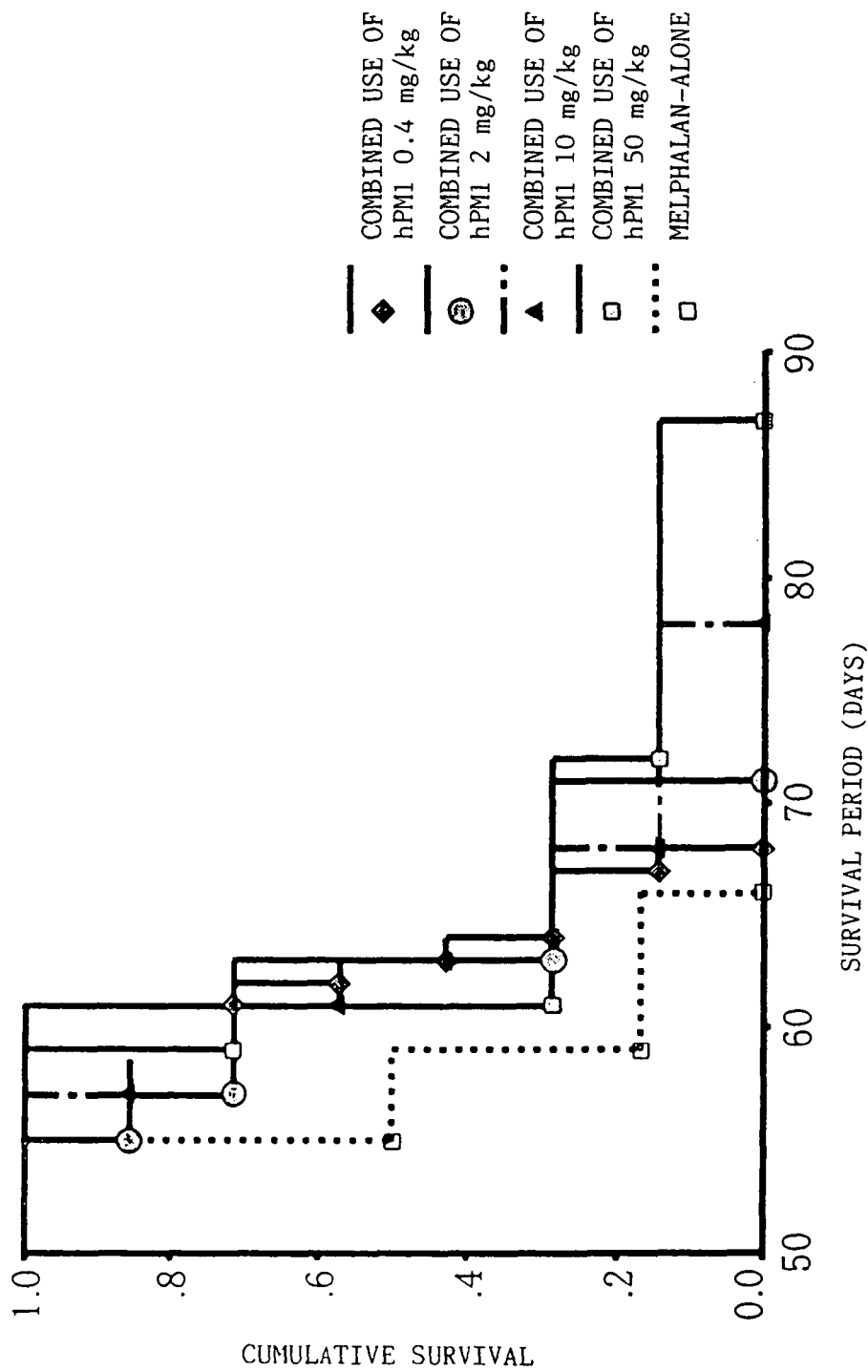
FIG. 14 is a graph showing the survival period by a survival curve of mice implanted with human myeloma cells in the melphalan single-drug administration group and the anti-human IL-6 receptor antibody (hPM1)-combined administration group, indicating an enhanced effect by combined use.
Figure 15:
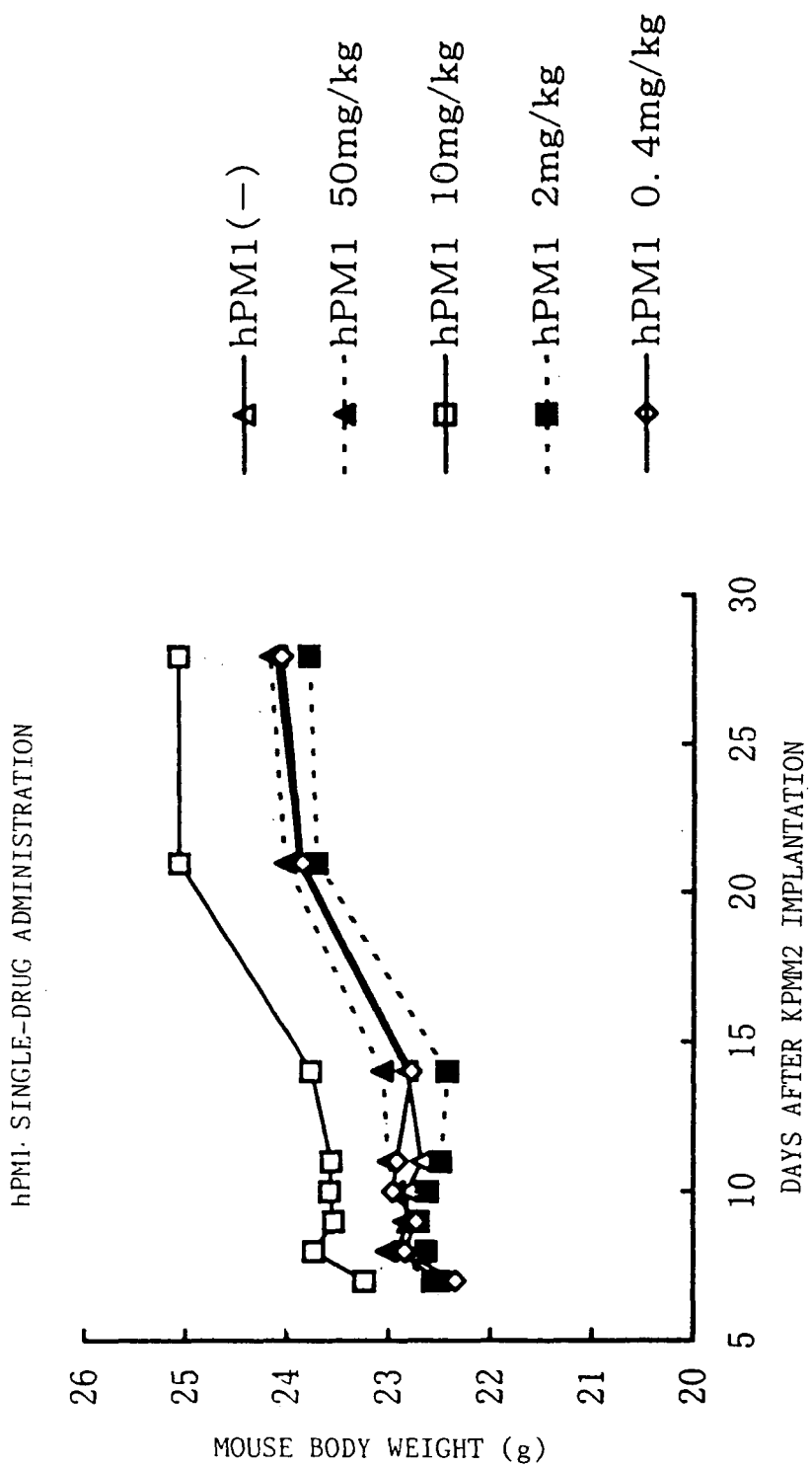
FIG. 15 is a graph showing the changes in body weight of mice implanted with human myeloma cells in the anti-human IL-6 receptor antibody single-drug administration group.
Figure 16:
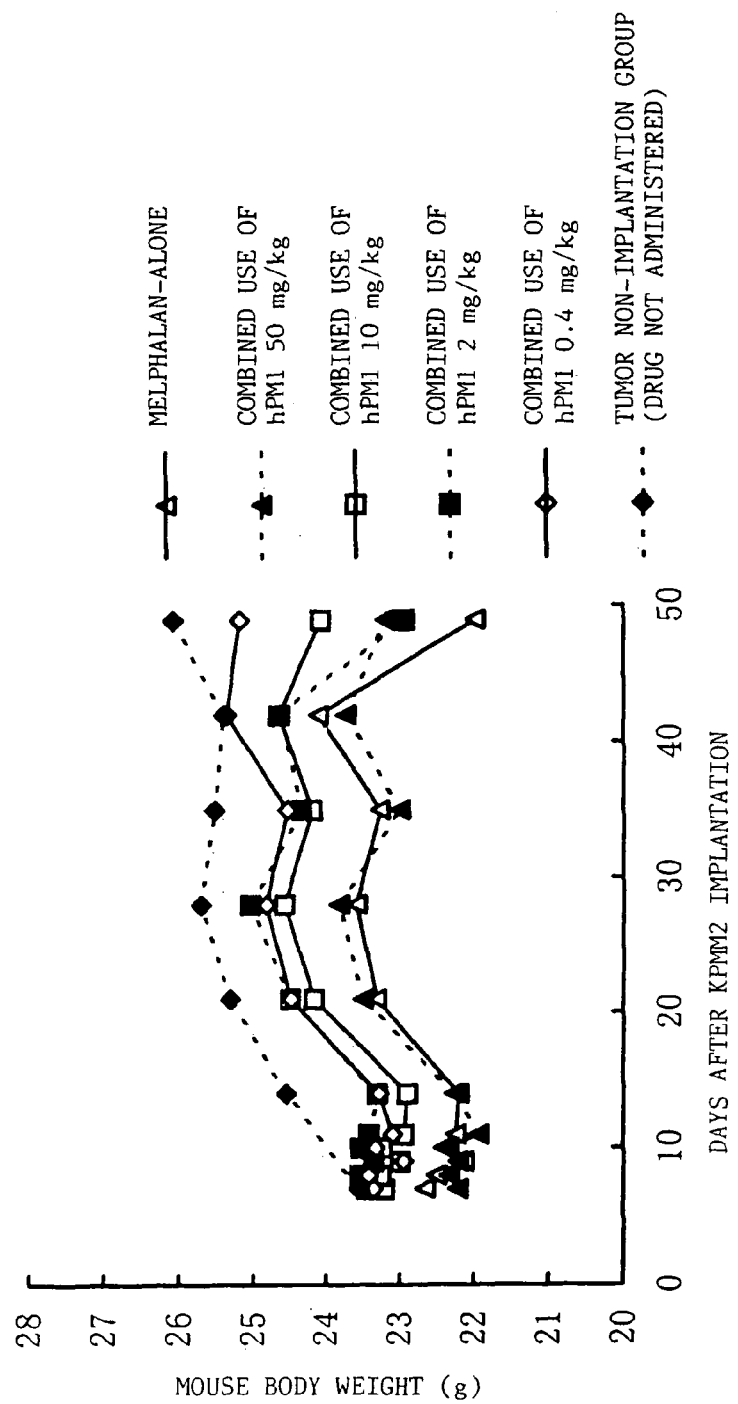
FIG. 16 is a graph showing the changes in body weight of mice implanted with human myeloma cells in the melphalan single-drug administration group and the anti-human IL-6 receptor antibody (hPM1)-combined administration group.

For the survival period, none of the doses in the antibody single-drug administration group gave a significant life elongation effect. Furthermore, melphalan alone has shown a significant life elongation effect, which was further enhanced by combined use of antibody (Table 2). At any dose, the life elongation effect tended to increase. Furthermore, in the 0.4 mg/kg and 50 mg/kg administration groups, significance was observed relative to the melphalan single-drug administration group in the generalized Wilcoxon's test (FIG. 14).

TABLE 2

Extension of survival period by combined use of
anti-human IL-6 receptor antibody hPM-1 and melphalan

| hPM-1 administration | Melphalan dosage | n | Survival period | Life-elongation ratio (%) |
|---|---|---|---|---|
| — | CMC control | 12 | 41.0 ± 1.7 | 100 |
| 50 mg/kg | CMC control | 7 | 41.6 ± 1.0 | 101 |
| 10 mg/kg | CMC control | 7 | 40.4 ± 1.7 | 99 |
| 2 mg/kg | CMC control | 7 | 41.4 ± 1.3 | 101 |
| 0.4 mg/kg | CMC control | 7 | 40.3 ± 1.2 | 98 |
| — | 1 mg/kg | 6 | 58.2 ± 1.8 | 142 (100) |
| 50 mg/kg | 1 mg/kg | 7 | 65.7 ± 3.9 | 160 (113) |
| 10 mg/kg | 1 mg/kg | 7 | 64.3 ± 2.7 | 157 (111) |
| 2 mg/kg | 1 mg/kg | 7 | 63.3 ± 2.3 | 154 (109) |
| 0.4 mg/kg | 1 mg/kg | 7 | 63.7 ± 1.1 | 155 (110) |

Life elongation ratio: 100×(drug administration group/drug non-administration group).

Values in the parentheses were obtained using the melphalan single-drug administration group as control.

Survival period was expressed as mean±standard error.

From the foregoing, it was demonstrated, the combined use of anti-IL-6 receptor antibody and melphalan has shown an antitumor effect at any dose from 0.4 mg/kg through 50 mg/kg.

The administration of melphalan caused toxicity to mice and inhibited body weight gain. When melphalan was used in combination with anti-human IL-6 receptor antibody, an antitumor effect was enhanced but toxicity (inhibition of body weight gain) was not expanded. Therefore, it was suggested that in the treatment of myeloma the administration of melphalan may be useful in enhancing effects, reducing the dosage, and breaking melphalan-resistance.

Reference to microorganisms deposited under Patent Cooperation Treaty Rule 13(2):

The name and address of the depository institute

Depository organization: the National Institute of Bioscience and Human Technology,
Agency of Industrial Science and Technology Address: 1-3, Higashi 1-chome, Tsukuba-shi, Ibaraki, Japan

| Accession No. | Date deposited |
|---|---|
| FERM BP-2998 | Jul. 10, 1990 |

Depository organization: National Collections of Industrial and Marine Bacteria Limited Address: 23 St Macher Drive, Aberdeen AB2 IRY, UNITED KINGDOM

| | |
|---|---|
| NCIMB 40366 | Feb. 11, 1991 |
| NCIMB 40362 | Feb. 11, 1991 |

What is claimed is:

1. A method for treating myeloma, comprising:
   (A) (a) providing an anti-IL-6 receptor antibody that inhibits signal transmission of IL-6 by blocking the binding of IL-6 ligand to IL-6 receptor,
   wherein an anticancer therapeutic mechanism of the anti-IL-6 receptor antibody is inhibition of signal transmission of IL-6;
   (b) providing a melphalan; and
   (c) administering the melphalan in combination with the anti-IL-6 receptor antibody as part of a treatment regimen,
   wherein the co-administration of melphalan and the anti-IL-6 receptor antibody has a higher (synergistic) therapeutic effect for myeloma than when the anti-IL-6 receptor antibody alone is administered or when the melphalan alone is administered; or
   (B) the method of (A), wherein the anti-IL-6 receptor antibody and the melphalan are formulated in separate pharmaceutical compositions which are administered at different times or are administered at the same time, or the anti-IL-6 receptor antibody and the melphalan are formulated in one pharmaceutical composition.

2. The method according to claim 1, wherein the anti-IL-6 receptor antibody comprises a monoclonal antibody.

3. The method according to claim 2, wherein the monoclonal antibody comprises a PM-1 antibody deposited as FERM BP-2998.

4. The method according to claim 3, wherein the PM-1 antibody comprises a reshaped human PM-1 antibody.

5. The method according to claim 1, wherein (a) the melphalan is administered as an oral administration of 1 to 20 mg per day, every day or 1 to 6 times per week, or as high-dose intravenous injection or infusion, single or multiple doses of 20 to 200 mg/m$^2$.

6. A method for treating myeloma, comprising
   (A) administering an anti-IL-6 receptor antibody in combination with a melphalan as part of a treatment regimen,
   wherein an anticancer therapeutic mechanism of the anti-IL-6 receptor antibody is inhibition of signal transmission of IL-6,
   and the anti-IL-6 receptor antibody or the melphalan is administered in an amount to have a higher (synergistic) therapeutic effect for myeloma than when the melphalan is administered alone, or when the anti-IL-6 receptor antibody is administered alone; or
   (B) the method of (A), wherein the anti-IL-6 receptor antibody and the melphalan are formulated in separate pharmaceutical compositions which are administered at different times or are administered at the same time, or the anti-IL-6 receptor antibody and the melphalan are formulated in one pharmaceutical composition.

7. The method according to claim 6, wherein the anti-IL-6 receptor antibody comprises a monoclonal antibody.

8. The method according to claim 7, wherein the monoclonal antibody comprises a PM-1 antibody deposited as FERM BP-2998.

9. The method according to claim 8, wherein the PM-1 antibody comprises a reshaped human PM-1 antibody.

10. The method according to claim 6, wherein melphalan is formulated for oral administration, or for oral administration at 1 to 20 mg per day, every day or 1 to 6 times per week, or for high-dose intravenous injection or infusion, single or multiple doses of 20 to 200 mg/m$^2$.

11. The method of claim 6, wherein the melphalan is administered as an oral administration of 1 to 20 mg per day, every day or 1 to 6 times per week, or as high-dose intravenous injection or infusion, single or multiple doses of 20 to 200 mg/m$^2$.

12. The method of claim 6, wherein the pharmaceutical composition is or the pharmaceutical compositions are administered simultaneously with the anti-IL-6 receptor antibody, and the ratio, is, when combined with daily oral administration of melphalan, 0.01 to 1000 fold (weight ratio) relative to the dose of melphalan.

13. The method of claim 1, wherein the pharmaceutical composition is or the pharmaceutical compositions are administered orally, by intravenous injection, drip infusion, intraarterial injection, intramuscular injection, intratumor injection, intrathoracic injection, or intraperitoneal injection, either systemically or locally.

14. The method of claim 1, wherein the pharmaceutical composition or the pharmaceutical compositions comprising anti-IL-6 receptor antibody is administered parenterally, by intravenous injection, drip infusion, intramuscular injection, intraperitoneal injection, subcutaneous injection, either systemically or locally; or, is administered as local dosage-forms, external preparations, local injections; or, as external preparations, liniments, ointments, gel, cream, emulsions, and liquids, tapes, plaster tapes, patches, nebulas, sprays or powders.

15. A method for treating a myeloma comprising:
   (A) (a) providing at least one pharmaceutical composition comprising separately or in combination:

(i) an anti-IL-6 receptor antibody that inhibits signal transmission of IL-6 by blocking the binding of IL-6 ligand to IL-6 receptor,
wherein an anticancer therapeutic mechanism of the anti-IL-6 receptor antibody is inhibition of signal transmission of IL-6, and
(ii) a melphalan; and
(b) administering to an individual in need thereof the pharmaceutical composition as part of a treatment regimen,
wherein the co-administration of melphalan and the anti-IL-6 receptor antibody has a higher (synergistic) therapeutic effect for myeloma than when the anti-IL-6 receptor antibody alone is administered or when the melphalan alone is administered; or
(B) the method of (A), wherein the anti-IL-6 receptor antibody and the melphalan are formulated in separate pharmaceutical compositions which are administered at different times or are administered at the same time, or the anti-IL-6 receptor antibody and the melphalan are formulated in one pharmaceutical composition.

16. The method of claim 1, wherein treating myeloma comprises a life elongation effect.

17. The method of claim 6, wherein treating myeloma comprises a life elongation effect.

18. The method of claim 15, wherein treating myeloma comprises a life elongation effect.

19. A method for treating a myeloma comprising:
(A) (a) providing at least one pharmaceutical composition comprising separately or in combination:
(i) a recombinant monoclonal anti-IL-6 receptor antibody that inhibits signal transmission of IL-6 by blocking the binding of IL-6 ligand to IL-6 receptor, and
(ii) a melphalan; and
(b) administering to an individual in need thereof the pharmaceutical composition as part of a treatment regimen, wherein the administration comprises at least in part intravenous administration of melphalan or the anti-IL-6 antibody,
wherein the co-administration of melphalan and the anti-IL-6 receptor antibody has a higher (synergistic) therapeutic effect for myeloma than when the anti-IL-6 receptor antibody alone is administered or when the melphalan alone is administered; or
(B) the method of (A), wherein the anti-IL-6 receptor antibody and the melphalan are formulated in separate pharmaceutical compositions which are administered at different times or are administered at the same time, or the anti-IL-6 receptor antibody and the melphalan are formulated in one pharmaceutical composition, and at least one of the formulations is an intravenous formulation.

* * * * *